US006197551B1

(12) United States Patent
Busfield

(10) Patent No.: US 6,197,551 B1
(45) Date of Patent: Mar. 6, 2001

(54) SPOIL-1 PROTEIN AND NUCLEIC ACID MOLECULES AND USES THEREFOR

(75) Inventor: Samantha J. Busfield, Cambridge, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/013,810

(22) Filed: Jan. 27, 1998

(51) Int. Cl.$^7$ .......................... C07H 21/04; C12N 5/00; C12N 15/63; C12N 15/85; C12P 21/04

(52) U.S. Cl. .................. 435/70.1; 435/71.1; 435/320.1; 435/325; 435/455; 536/24.3; 536/23.5

(58) Field of Search .............................. 435/70.1, 71.1, 435/320.1, 325, 455; 536/23.5, 24.3

(56) References Cited

U.S. PATENT DOCUMENTS 5,863,769  1/1999  Young.

FOREIGN PATENT DOCUMENTS

0121338 * 3/1984 (EP).
0 855 404 A1 7/1998 (EP).

OTHER PUBLICATIONS

Marra et al. GenBank Accession No. AA030324, Jan. 21, 1997.*

Cominelli, F. et al., "Rabbit interleukin–1 receptor antagonist: Cloning, expression, functional characterization, and regulation during intestinal inflammation," *J. Biol. Chem.*, 269: 6962–6971, vol. 9 (1994).

Lacey, D. et al., "Interleukin 4, Interferon–γ, and Prostaglandin E Impact the Osteoclastic Cell–Forming Potential of Murine Bone Marrow Macrophages," *Endocrinology*, vol. 136, No. 6, 2367–76 (1995).

Lennard, A. et al., "Cloning and Chromosome Mapping of the Human Interleukin–1 Receptor Antagonist Gene," *Cytokine*, vol. 4, No. 2, 83–9 (1992).

Lorenzo, J. et al., "Comparison of the Bone–Resorbing Activity in the Supernatants from Phytohemagglutinin–Stimulated Human Peripheral Blood Mononuclear Cells with that of Cytokines Through the use of an Antiserum to Interleukin 1," *Endocrinology*, vol. 121, No. 3, 1164–70 (1987).

Muzio, M. et al., "Cloning and Characterization of a New Isoform of the Interleukin 1 Receptor Antagonist," *J. Exp. Med.*, vol. 182, No. 2, 623–8 (1995).

Ohlsson, K. et al., "Interleukin–1 Receptor Antagonist Reduces Mortality from Endotoxin Shock," *Nature*, vol. 348, 550–6 (1990).

Pacifici, R. et al., "Monocytic Secretion of Interleukin–1 Receptor Antagonist in Normal and Osteoporotic Women: Effects of Menopause and Estrogen/ Progesterone Therapy," *J. Clin. Endocrinol. Metab.*, vol. 77, No. 5, 1135–41 (1993).

Rambaldi, A. et al., "Expression of Leukocyte Alkaline Phosphatase Gene in Normal and Leukemic Cells: Regulation of the Transcript by Granulocyte Colony–Stimulating Factor," *Blood*, vol. 76, 114–20 (1990).

Shuck, M.E. et al. "Cloning heterologous expression and characterization of murine interleukin 1 receptor antagonist protein," *Eur. J. Immunol.*, vol. 21, 2775–2780 (1991).

Udagawa, N. et al., "The Bone Marrow–Derived Stromal Cell Lines MC3T3–G2/PA6 and ST2 Support Osteoclast–Like Cell Differentiation in Cocultures with Mouse Spleen Cells," *Endocrinology*, vol. 125, No. 3, 1805–13 (1989).

Weissbach, L. et al., "Detection of an Interleukin–1 Intracellular Receptor Antagonist mRNA Variant," *Biochem. Biophys. Res. Commun.*, vol. 244, 91–5 (1998).

Dinarello, C., "Interleukin–1 Antagonism", *Blood*, vol. 77, no. 8, 1627–52 (1991).

Eisenberg, S.P. et al., "Interleukin 1 receptor anagonist is a member of the interleukin 1 gene family: Evolution of a cytokine control mechanism", *PNAS USA*, vol. 88, 5232–5236 (1991).

Eisenberg S.P. et al., "Primary Structure and Functional Expression from Complementary DNA of a Human Interleukin–1 Receptor Antagonist", *Nature*, vol. 343, no. 6256, 341–6 (1990).

GenBank®Accession Number W78043 for Human IL–1Ra Protein Precursor cDNA, Est;

GenBank®Accession Number AA030324 fro Murine Mus Musculus cDNA, Est;

Gowen, M. et al., "An Interleukin 1 Like Factor Stimulates Bone Resorption in Vitro", *Nature*, vol. 306, 378–80 (1983).

Haskill, S. ET AL., "cDNA Cloning of an Intracellula Form of the Human Interleukin 1 Receptor Antagonist Associated with Epithelium", *PNAS*, vol. 88 no. 9, 3681–5 (1991).

Hawley, R. et al., "Versatile Retroviral Vectors for Potential use in Gene Therapy", vol. 1 136–8 (1994).

Horowitz, M. and Lorenzo, J., "Local Regulators of Bone: IL–1, TNF, Lymphotoxin, Interferon–γ, IL–8, IL–10, IL–4, the LIF/IL–6 Family, and Additional Cytokines", *Priniciples of Bone Biology*, ch. 49, 687–700 (1996).

Jenkins, J.K. et al. "Intracellular IL–1 Receptor Antagonist Promoter: Cell Type–Specific and Inducible Regulatory Regions", *J. Immunol.*, vol. 158, no. 2, 748–55 (1997).

Ju, G. et al. "Conversion of the Interleukin 1 Receptor Antagonists into an Agonist by Site–specific Mutagenesis", *PNAS*, vol. 88, 2658–62 (1991).

Kato, H. et al., "Molecular cloning and functional expression of equine interleukin–1 receptor antagonist", *Veterinary Immunology and Immunopathy*, vol. 56, 221–231 (1997).

\* cited by examiner

*Primary Examiner*—Karen Hauda
*Assistant Examiner*—Anne-Marie Baker
(74) *Attorney, Agent, or Firm*—Lahive & Cockfield, LLP; DeAnn Smith; Debra J. Milasincic

(57) ABSTRACT

Novel SPOIL-1 polypeptides, proteins, and nucleic acid molecules are disclosed. In addition to isolated, full-length SPOIL-1 proteins, the invention further provides isolated SPOIL-1 fusion proteins, antigenic peptides and anti-SPOIL-1 antibodies. The invention also provides SPOIL-1 nucleic acid molecules, recombinant expression vectors containing a nucleic acid molecule of the invention, host cells into which the expression vectors have been introduced and non-human transgenic animals in which a SPOIL-1 gene has been introduced or disrupted. Diagnostic, screening and therapeutic methods utilizing compositions of the invention are also provided.

16 Claims, 5 Drawing Sheets

FIG. 1

Nucleotide and Amino Acid Sequence of Spoil-1

```
GAATTCGGCACGAGGGTAGTGTGCAGACACATTCCTATTCAATCAGGGTCAATCTGCAGATTGGCAGCTCAGAAACAAC            79

M   F   R   I   L   V        6
ATCACCATAATGAATAAGGAGAAAGAACTAAGAGCAGCATCACCTTCGCTTAGAC ATG TTC AGG ATC TTA GTA          152

V   V   C   G   S   C   R   T   I   S   S   L   Q   S   Q   G   K   S   K   Q          26
GTC GTG TGT GGA TCC TGC AGA ACA ATA TCC TCA CTG CAG TCC CAA GGA AAG AGC AAA CAG          212

F   Q   E   G   N   I   M   E   M   Y   N   K   K   E   P   V   K   A   S   L          46
TTC CAG GAA GGG AAC ATA ATG GAA ATG TAC AAC AAA AAG GAA CCT GTA AAA GCC TCT CTC          272

F   Y   H   K   S   G   T   S   T   T   F   E   S   A   A   F   P   G   W              66
TTC TAT CAC AAG AGT GGT ACA AGC ACC TTT GAG TCT GCA GCC TTC CCT GGT TGG                  332

F   I   A   V   C   S   K   G   S   C   P   L   I   L   T   Q   L   G   E              86
TTC ATC GCT GTC TGC TCT AAA GGG AGC TGC CCA CTC ATT CTG ACC CAA GAA CTG GGG GAA          392

I   F   I   T   D   F   E   M   I   V   V   H   *                                       99
ATC TTC ATC ACT GAC TTC GAG ATG ATT GTG GTA CAT TAA                                     431

GGTTTTTAGACACATTGCTCTGTGGCACTCTCTCTCAAGATTCTTTGGATTCTAACAAGAAGCAATCAAAGACACACCCCTAA     510
CAAAATGGAAGACTGAAAGAAGAACTGAGCCCTCCCCTTGGCTGTTTTTCCTTGGTGGTGAATCAGATGAAGAACATCTT        589
ACCATGTTTCATCCAAAGCATTTACTGTGGTTTTACAAGGAGTGAATTTTTAAAATAAAATCATTTATCTCATAA             668
AAAAAAAAAAAAAAAAAAAAAAAAAAAAAAAAAAAAAAAAAAAAAAAAAAAAAAAAAAAAAAAAAACTCTCGCGGCCGC         746
```

FIG. 2

Nucleotide Sequence and Amino Acid Sequence of Mature SpoIl-1

```
L   Q   S   Q   G   K   S   K   Q   F   Q   E   G   N   I   M   E   M   Y   N      20
CTG CAG TCC CAA GGA AAG AGC AAA CAG TTC CAG GAA GGG AAC ATA ATG GAA ATG TAC AAC     60

K   K   E   P   V   K   A   S   L   F   Y   H   Y   K   K   S   G   T   S   T      40
AAA AAG GAA CCT GTA AAA GCC TCT CTC TTC TAT CAC AAG AGT ACA ACC TCT ACA            120

F   E   S   A   A   F   P   G   W   F   I   A   V   C   S   K   G   S   C   P      60
TTT GAG TCT GCA GCC TTC CCT GGT TGG TTC ATC GCT GTC TGC TCT AAA GGG AGC TGC CCA    180

L   I   L   T   Q   E   L   Q   E   I   F   I   T   D   F   E   M   I   V   V      80
CTC ATT CTG ACC CAA GAA CTG GGG GAA ATC TTC ATC ACT GAC TTC GAG ATG ATT GTG GTA    240

H   *   81
CAT TAA 243
```

Alignment of Murine SPOIL-1 with Murine IL-1α, IL-1β and IL-Ira

FIG. 3B

SPOIL-1 PROTEIN AND NUCLEIC ACID MOLECULES AND USES THEREFOR

BACKGROUND OF THE INVENTION

Interleukin-1 (IL-1) is a multifunctional cytokine which comprises a family of two polypeptides, IL-1α and IL-1β, with a wide spectrum of activities. IL-1α and IL-1 β have been found to possess inflammatory, metabolic, physiologic, hematopoeitic and immunologic properties. Although both forms of IL-1 are distinct gene products, they recognize the same cell surface receptors (i.e. IL-1 receptors, IL-1RtI and IL-1RtII).

Besides skin keratinocytes, some epithelial cells and certain cells in the central nervous system, significant amounts of mRNA encoding IL-1 are not observed in most other healthy cells. However, IL-1 production is dramatically increased by a variety of cells in response to infection, microbial toxins, inflammatory agents, products of activated lymphocytes, complement and clotting components. In addition, IL-1 has been recognized as a prototype of proinflammatory cytokines in that it induces the expression of a variety of genes and the synthesis of several proteins that in turn, induce acute and chronic inflammation. Thus, circulating IL-1 has been implicated in various disease states including sepsis, rheumatoid arthritis, stroke and diabetes. Dinarello (1991) *Blood* 77(8):1627–1652.

In addition, IL-1 has been shown to regulate bone reabsorption and bone formation with its major activity in bone metabolism being osteoclast activation. See Gowen et al. (1983) *Nature* 306:378–380. In fact, IL-1 has been reported to be a potent stimulator of bone reabsorption and has also been reported to increase prostaglandin synthesis in bone. Lorenzo et al. (1987) *Endocrinology* 121:1164–1170.

A natural occurring inhibitor of IL-1 which specifically inhibits IL-1 activity has also been identified. Carter et al. (1990) *Nature* 344:633. This protein, called IL-1 receptor antagonist protein (IL-1ra), has been shown to compete with the binding of IL-1 to its surface receptors. Thus, significant interest has arisen in administering IL-1ra to block the activity of IL-1 in various diseases including septic shock (Ohlsson et al. (1990) *Nature* 348:550–556), immune complex-induced colitis (Cominelli (1990) *J. Clin. Invest.* 86:972–979), acute myelogenous leukemia (Rambaldi et al. (1990) *Blood* 76:114–120) and osteoporosis (Pacifici et al. (1993) *J. Clin. Endocrinol. Metab.* 77:1135–1141).

SUMMARY OF THE INVENTION

The present invention is based, at least in part, on the discovery of novel IL-1 receptor antagonist (IL-1ra) -like molecules, referred to herein as SPOIL-1 nucleic acid and protein molecules. The SPOIL-1 molecules of the present invention are useful as modulating agents in regulating a variety of cellular processes. Accordingly, in one aspect, this invention provides isolated nucleic acid molecules encoding SPOIL-1 proteins and biologically active portions thereof, as well as nucleic acid fragments suitable as primers or hybridization probes for the detection of SPOIL-1-encoding nucleic acids.

In one embodiment, a SPOIL-1 nucleic acid molecule is 65% homologous to the nucleotide sequence shown in SEQ ID NO:3, SEQ ID NO:4, or a complement thereof In a preferred embodiment, an isolated SPOIL-1 nucleic acid molecule encodes the amino acid sequence of murine SPOIL-1.

In another embodiment, a SPOIL-1 nucleic acid molecule further comprises nucleotides 135–431 of SEQ ID NO:1. In yet another preferred embodiment, a SPOIL-1 nucleic acid molecule further comprises nucleotides 186–431 of SEQ ID NO:1.

In yet another preferred embodiment, an isolated SPOIL-1 nucleic acid molecule has the nucleotide sequence shown SEQ ID NO:3 or SEQ ID NO:4.

In another embodiment, a SPOIL-1 nucleic acid molecule includes a nucleotide sequence encoding a protein having an amino acid sequence sufficiently homologous to the amino acid sequence of SEQ ID NO:2 or SEQ ID NO:5. In yet another embodiment, a SPOIL-1 nucleic acid molecule includes a nucleotide sequence encoding a protein having an amino acid sequence at least 60% homologous to the amino acid sequence of SEQ ID NO:2 or SEQ ID NO:5. In a preferred embodiment, a SPOIL-1 nucleic acid molecule includes a nucleotide sequence encoding a protein having the amino acid sequence of SEQ ID NO:2 or SEQ ID NO:5.

In another embodiment, an isolated nucleic acid molecule of the present invention encodes a SPOIL-1 protein which includes an interleukin-1 (IL-1) signature domain, optionally, a signal sequence and is secreted. In another embodiment, an isolated nucleic acid molecule of the present invention encodes a SPOIL-1 protein which includes an IL-1 signature domain and has SPOIL-1 biological activity. The SPOIL-1 nucleic acid molecule can also encode a SPOIL-1 protein and is a naturally occurring nucleotide sequence. In yet another embodiment, an isolated nucleic acid molecule of the present invention encodes a SPOIL-1 protein and comprises a nucleotide sequence which hybridizes under stringent hybridization conditions to a nucleic acid molecule having the nucleotide sequence of SEQ ID NO:3 or SEQ ID NO:4.

In another embodiment, the SPOIL-1 nucleic acid molecule is at least 500 nucleotides in length and hybridizes under stringent conditions to a nucleic acid molecule comprising the nucleotide sequence shown in SEQ ID NO:3, SEQ ID NO:4, or a complement thereof Another embodiment the invention provides an isolated nucleic acid molecule which is antisense to the coding strand of a SPOIL-1 nucleic acid.

Another aspect of the invention provides a vector comprising a SPOIL-1 nucleic acid molecule. In certain embodiments, the vector is a recombinant expression vector. In a preferred embodiment, the vector comprises the SPOIL-1 nucleic acid sequence of SEQ ID NO:3 or SEQ ID NO:4. In another embodiment, the invention provides a host cell containing a vector of the invention. The invention also provides a method for producing SPOIL-1 protein by culturing in a suitable medium, a host cell of the invention containing a recombinant expression vector such that SPOIL-1 protein is produced.

Another aspect of this invention features isolated or recombinant SPOIL-1 proteins and polypeptides. In one embodiment, an isolated SPOIL-1 protein has an IL-1 signature domain, optionally, a signal sequence, and is secreted. In another embodiment, an isolated SPOIL-1 protein has an IL-1 signature domain and a SPOIL-1 biological activity. In yet another embodiment, an isolated SPOIL-1 protein has an amino acid sequence sufficiently homologous to the amino acid sequence of SEQ ID NO:2 or SEQ ID NO:5. In a preferred embodiment, a SPOIL-1 protein has an amino acid sequence at least about 60% homologous to the amino acid sequence of SEQ ID NO:2 or SEQ ID NO:5. In another embodiment, a SPOIL-1 protein has the amino acid sequence of SEQ ID NO:2 or SEQ ID NO:5.

Another embodiment of the invention features an isolated SPOIL-1 protein which is encoded by a nucleic acid molecule having a nucleotide sequence at least about 65% homologous to a nucleotide sequence of SEQ ID NO:3, SEQ ID NO:4, or a complement thereof. This invention also features an isolated SPOIL-1 protein which is encoded by a nucleic acid molecule having a nucleotide sequence which hybridizes under stringent hybridization conditions to a nucleic acid molecule comprising the nucleotide sequence of SEQ ID NO:3, SEQ ID NO:4, or a complement thereof.

The SPOIL-1 proteins of the present invention, or biologically active portions thereof, can be operatively linked to a non-SPOIL-1 polypeptide to form SPOIL-1 fusion proteins. The invention further features antibodies that specifically bind SPOIL-1 proteins, such as monoclonal or polyclonal antibodies. In addition, the SPOIL-1 proteins or biologically active portions thereof can be incorporated into pharmaceutical compositions, which optionally include pharmaceutically acceptable carriers.

In another aspect, the present invention provides a method for detecting SPOIL-1 expression in a biological sample by contacting the biological sample with an agent capable of detecting a SPOIL-1 nucleic acid molecule, protein or polypeptide such that the presence of SPOIL-1 nucleic acid molecule, protein or polypeptide is detected in the biological sample.

In another aspect, the present invention provides a method for detecting the presence of SPOIL-1 activity in a biological sample by contacting the biological sample with an agent capable of detecting an indicator of SPOIL-1 activity such that the presence of SPOIL-1 activity is detected in the biological sample.

In another aspect, the invention provides a method for modulating SPOIL-1 activity comprising administering an agent that modulates SPOIL-1 activity such that SPOIL-1 activity in the cell is modulated. In one embodiment, the agent inhibits SPOIL-1 activity. In another embodiment, the agent stimulates SPOIL-1 activity. In one embodiment, the agent is an antibody that specifically binds to SPOIL-1 protein. In another embodiment, the agent modulates expression of SPOIL-1 by modulating transcription of a SPOIL-1 gene or translation of a SPOIL-1 mRNA. In yet another embodiment, the agent is a nucleic acid molecule having a nucleotide sequence that is antisense to the coding strand of the SPOIL-1 mRNA or the SPOIL-1 gene.

In another aspect, the invention provides a method for modulating IL-1 activity comprising administering a SPOIL-1 agent that modulates IL-1 activity such that IL-1 activity in the cell is modulated. In one embodiment, a SPOIL-1 agent inhibits or reduces IL-1 activity. Thus, in one embodiment, the SPOIL-1 agent is a SPOIL-1 protein or biologically active portion thereof which functions as an IL-1 receptor antagonist. In another embodiment, a SPOIL-1 agent stimulates IL-1 activity. Thus, in another embodiment, the SPOIL-1 agent is a SPOIL-1 protein or biologically active portion thereof which functions as an IL-1 agonist.

In one embodiment, the methods of the present invention are used to treat a subject having a disorder characterized by aberrant IL-1 expression or activity by administering a SPOIL-1 agent which is an IL-1 modulator to the subject. In one embodiment, the SPOIL-1 agent is a SPOIL-1 protein. In yet another embodiment, the SPOIL-1 agent is a peptide or peptidomimetic. In a preferred embodiment, the disorder characterized by aberrant IL-1 protein expression is a bone metabolism disorder, or a proinflammatory disorder.

The present invention also provides a diagnostic assay for identifying the presence or absence of a genetic alteration characterized by at least one of (i) aberrant modification or mutation of a gene encoding a SPOIL-1 protein; (ii) misregulation of said gene; and (iii) aberrant post-translational modification of a SPOIL-1 protein, wherein a wild-type form of said gene encodes an protein with a SPOIL-1 activity.

Other features and advantages of the invention will be apparent from the following detailed description and claims.

BRIEF DESCRIPTION OF THE DRAWINGS

FIG. 1 depicts the cDNA sequence and predicted amino acid sequence of murine SPOIL-1. The nucleotide sequence corresponds to nucleic acids 1 to 746 of SEQ ID NO:1. The amino acid sequence corresponds to amino acids 1 to 98 of SEQ ID NO:2.

FIG. 2 depicts the cDNA sequence encoding a mature murine SPOIL-1 protein (nucleic acids 1–246 of SEQ ID NO:4) and the corresponding amino acid sequence (amino acid residues 1–81 of SEQ ID NO: 5).

DETAILED DESCRIPTION OF THE INVENTION

Figure 3A:
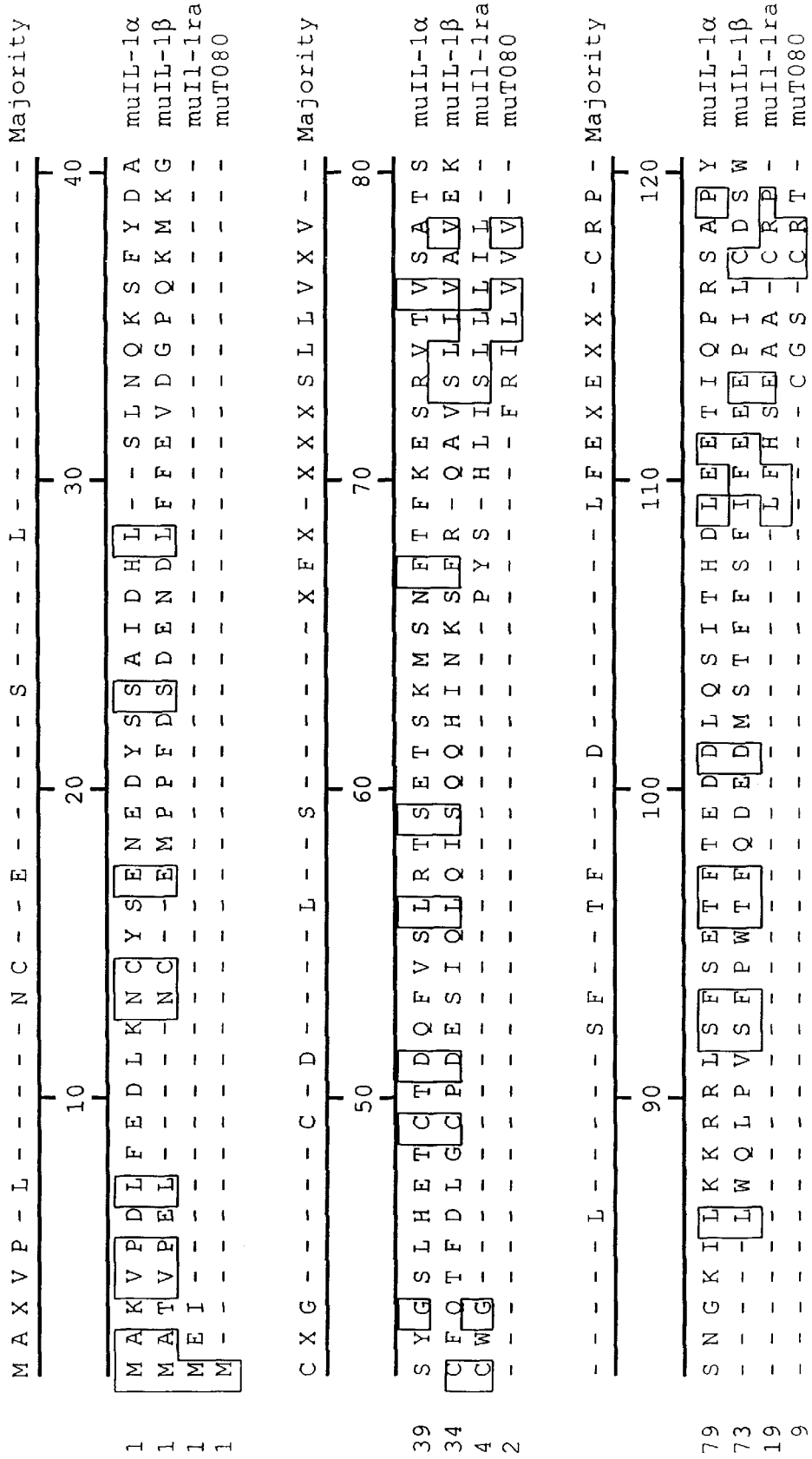
FIG. 3 depicts an alignment of the amino acid sequence of murine SPOIL-1 (also refered to as murine or mTANGO 080) (corresponding amino acids 1 to 98 of SEQ ID NO:2), murine IL-1ra (Swissprot™ Accession Number P25085), murine IL-1α (Swissprot™ Accession Number P01582) and murine IL-1β (Swissprot™ Accession Number P10749).

The present invention is based on the discovery of novel molecules having homology to members of the IL-1 receptor antagonist (IL-1ra) family, referred to herein as SPOIL-1 protein and nucleic acid molecules, which comprise a family of molecules having certain conserved structural and functional features. The nucleotide sequences of murine SPOIL-1 nucleic acid molecules and the amino acid sequence of the respective murine SPOIL-1 protein molecules are depicted in FIGS. 1 and 2.

The term "family" when referring to the protein and nucleic acid molecules of the invention is intended to mean two or more protein or nucleic acid molecules having a common structural domain and having sufficient amino acid or nucleotide sequence homology as defined herein. Such family members can be naturally occurring and can be from either the same or different species. For example, a family can contain a first protein of human origin and a homologue of that protein of murine origin, as well as a second, distinct protein of human origin and a murine homologue of that protein. Members of a family may also have common functional characteristics.

In one embodiment, a SPOIL-1 family member is identified based on the presence of an "IL-1 signature domain" in the protein or corresponding nucleic acid molecule. As used herein, the term "IL-1 signature domain" refers to a protein domain which contains a conserved motif of a SPOIL-1 protein member (or IL-1ra or IL-1 family member) and is at least about 10–30 amino acid residues, preferably about 15–25 amino acid residues, more preferably about 17–24 amino acid residues, more preferably 19–23 amino acid residues, and more preferably 21–22 amino acid residues in length. An IL-1 signature domain preferably includes the following amino acid sequence motif: F-$Xaa_1$-S-A-$Xaa_2$-$Xaa_3$-P-$Xaa_4$-$Xaa_5$$Xaa_n$-L, wherein Xaa represents any amino acid, and n is about 5–25 amino acid residues, more preferably about 6–18 amino acid residues, and more preferably about 6–15 amino acid residues (SEQ ID NO:6). In a preferred embodiment, the IL-1 signature domain includes the following amino acid sequence: F-Xaa$_1$-S-A-Xaa$_2$-Xaa$_3$-P-Xaa$_4$-Xaa$_5$Xaa$_n$-L, wherein Xaa$_1$ is either threonine (T) or glutamic acid (E); Xaa$_2$ is either alanine (A) or glutamic acid (E); and Xaa$_5$ is either tryptophan (W) or leucine (L) (SEQ ID NO:7) In another embodiment, the IL-1 signature domain is at least about 10–30 amino acid residues in length, preferably 15–25 amino acid residues in length, preferably 17–24 amino acid residues, 19–23 amino acid residues or more preferably 21–22 amino acid residues in length and has at least about 30–60% homology, preferably at least about 35–55% homology, more preferably at least about 40–50% homology, and more preferably at least about 46–49% homology with an IL-1 signature domain of a SPOIL-1 protein having an amino acid sequence as set forth in SEQ ID NO:2 (e.g., amino acid residues 58–80) or SEQ ID NO:5 (e.g., amino acid residues 41–63).

In a preferred embodiment, a SPOIL-1 protein contains an IL-1 signature domain of SEQ ID NO:2 (e.g., amino acid residues 58–80). In another embodiment, a SPOIL-1 protein contains a IL-1 signature domain of SEQ ID NO:5 (e.g., amino acid residues 41–63). Another embodiment of the invention features SPOIL-1 molecules which contain a signal sequence. As used herein, a "signal sequence" refers to a peptide containing about 17 amino acids which occurs at the N-terminus of secretory proteins and which contains a large number of hydrophobic amino acid residues. For example, a signal sequence contains at least about 13–22 amino acid residues, preferably about 15–20 amino acid residues, more preferably about 16–19 amino acid residues, and more preferably about 17 amino acid residues, and has at least about 35–65%, preferably about 38–50%, and more preferably about 40–45% hydrophobic amino acid residues (e.g., Valine, Leucine, Isoleucine or Phenylalanine). Such a "signal sequence", also referred to in the art as a "signal peptide", serves to direct a protein containing such a sequence to a lipid bilayer. For example, in one embodiment, a SPOIL-1 protein contains a signal sequence containing about amino acids 1–17 of SEQ ID NO:2.

In a preferred embodiment, a SPOIL-1 protein contains both an IL-1 signature domain and a signal sequence. In one exemplary embodiment, a SPOIL-1 protein contains an IL-1 signature domain comprising amino acids 58–80 of SEQ ID NO:2 which further contains a signal sequence at amino acids 1–17 of SEQ ID NO:2.

In yet another embodiment, a SPOIL-1 protein encodes a mature SPOIL-1 protein. As used herein, the term "mature SPOIL-1 protein" refers to a SPOIL-1 protein from which the signal peptide has been cleaved. In an exemplary embodiment, a mature SPOIL-1 protein contains amino acid residues 1 to 81 of SEQ ID NO:5. In a preferred embodiment, a SPOIL-1 protein is a mature SPOIL-1 protein which comprises an IL-1 signature domain.

Preferred SPOIL-1 molecules of the present invention have an amino acid sequence sufficiently homologous to the amino acid sequence of SEQ ID NO:2 or SEQ ID NO:5. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains and/or a common functional activity. For example, amino acid or nucleotide sequences which share common structural domains have at least about 40% homology, preferably 50% homology, more preferably 60%–65% homology, and even more preferably 70% across the amino acid sequences of the domains and contain at least one structural domain, are defined herein as sufficiently homologous. Furthermore, amino acid or nucleotide sequences which share at least 40%, preferably 50%, more preferably 60, 65, 70, or 80% homology and share a common functional activity are defined herein as sufficiently homologous.

As used interchangeably herein a "SPOIL-1 activity", "biological activity of SPOIL-1 " or "functional activity of SPOIL-1 ", refers to an activity exerted by a SPOIL-1 protein, polypeptide or nucleic acid molecule on a SPOIL-1 responsive cell as determined in vivo, or in vitro, according to standard techniques. In one embodiment, a SPOIL-1 activity is a direct activity, such as an association with a cell-surface protein (e.g., a IL-1 receptor) or a SPOIL-1 target molecule. In another embodiment, a SPOIL-1 activity is an indirect activity, such as the inhibiting synthesis of a second protein (e.g. a protein of a signal pathway) by interaction of the SPOIL-1 protein with a cell surface protein or a SPOIL-1 target molecule. In a preferred embodiment, a SPOIL-1 activity is at least one or more of the following activities: (i) interaction of a SPOIL-1 protein in the extracellular millieu with a non-SPOIL-1 protein molecule on the surface of the same cell which secreted the SPOIL-1 protein molecule; (ii) interaction of a SPOIL-1 protein in the extracellular millieu with a non-SPOIL-1 protein molecule on the surface of a different cell from that which secreted the SPOIL-1 protein molecule; (iii) complex formation between a SPOIL-1 protein and an IL-1 receptor; and (iv) interaction of a SPOIL-1 protein with a second protein in the extracellular millieu. In yet another preferred embodiment, a SPOIL-1 activity is at least one or more of the following activities: (i) inhibiting an IL-1 -dependent signal transduction pathway; (ii) modulating secretion of a non-IL-1 cytokine; (iii) modulating secretion of IL-1; (iv) competing with IL-1 to bind an IL-1 receptor; (v) modulating a proinflammatory cytokine; (vi) modulating IL-1-stimulation of cell development or differentiation; (vii) modulating bone metabolism (e.g., bone formation and reabsorption).

Accordingly, another embodiment of the invention features isolated SPOIL-1 proteins and polypeptides having a SPOIL-1 activity. Preferred SPOIL-1 proteins have an IL-1 signature domain and a SPOIL-1 activity. In another embodiment, the SPOIL-1 protein has a signal peptide, an IL-1 signature domain, and a SPOIL-1 activity. In another preferred embodiment, the SPOIL-1 protein has a signal peptide, an IL-1 signature domain, a SPOIL-1 activity, and an amino acid sequence sufficiently homologous to an amino acid sequence of SEQ ID NO:2. In another preferred embodiment, the SPOIL-1 protein has an IL-1 signature domain, a SPOIL-1 activity, and an amino acid sequence sufficiently homologous to an amino acid sequence of SEQ ID NO:5.

In a particularly preferred embodiment, the SPOIL-1 protein and nucleic acid molecules of the present invention are murine SPOIL-1 molecules. A nucleotide sequence of the isolated murine SPOIL-1 cDNA and the predicted amino acid sequence of the murine SPOIL-1 protein are shown in FIG. 1 and in SEQ ID NOs:1 and 2, respectively. In addition, the nucleotide sequences corresponding to the coding region of the murine SPOIL-1 cDNA (nucleotides 135–431) and the SPOIL-1 cDNA encoding the mature SPOIL-1 protein are represented as SEQ ID NO:3 and SEQ ID NO:4, respectively.

The murine SPOIL-1 cDNA (set forth in SEQ ID NO:I), which is approximately 746 nucleotides in length, encodes a protein having a molecular weight of approximately 10.96 kD (with signal sequence) and 9.1 kD (without signal sequence) and which is approximately 98 amino acid residues in length (SEQ ID NO:2). The murine SPOIL-1 protein contains an IL-1 signature domain as defined herein. A SPOIL-1 IL-1 signature domain can be found, for example, from about amino acids 58 to 80 of SEQ ID NO:2 and, for example, from about amino acids 41–63 of SEQ ID NO:5. In addition, the murine SPOIL-1 protein can contain a signal sequence. A signal sequence can be found at least, for example, from about amino acids 1–17 of SEQ ID NO:2. The prediction of such a signal peptide can be made, for example, utilizing the computer algorithm SignalP (Henrik, et al. (1997) *Protein Engineering* 10:1–6).

In situ hybridization was performed and murine SPOIL-1 expression was observed exclusively in the squamous cell epithelium of the esophagus and the epithelial lining of the mouth in both adult and embryonic tissues.

Figure 3B:
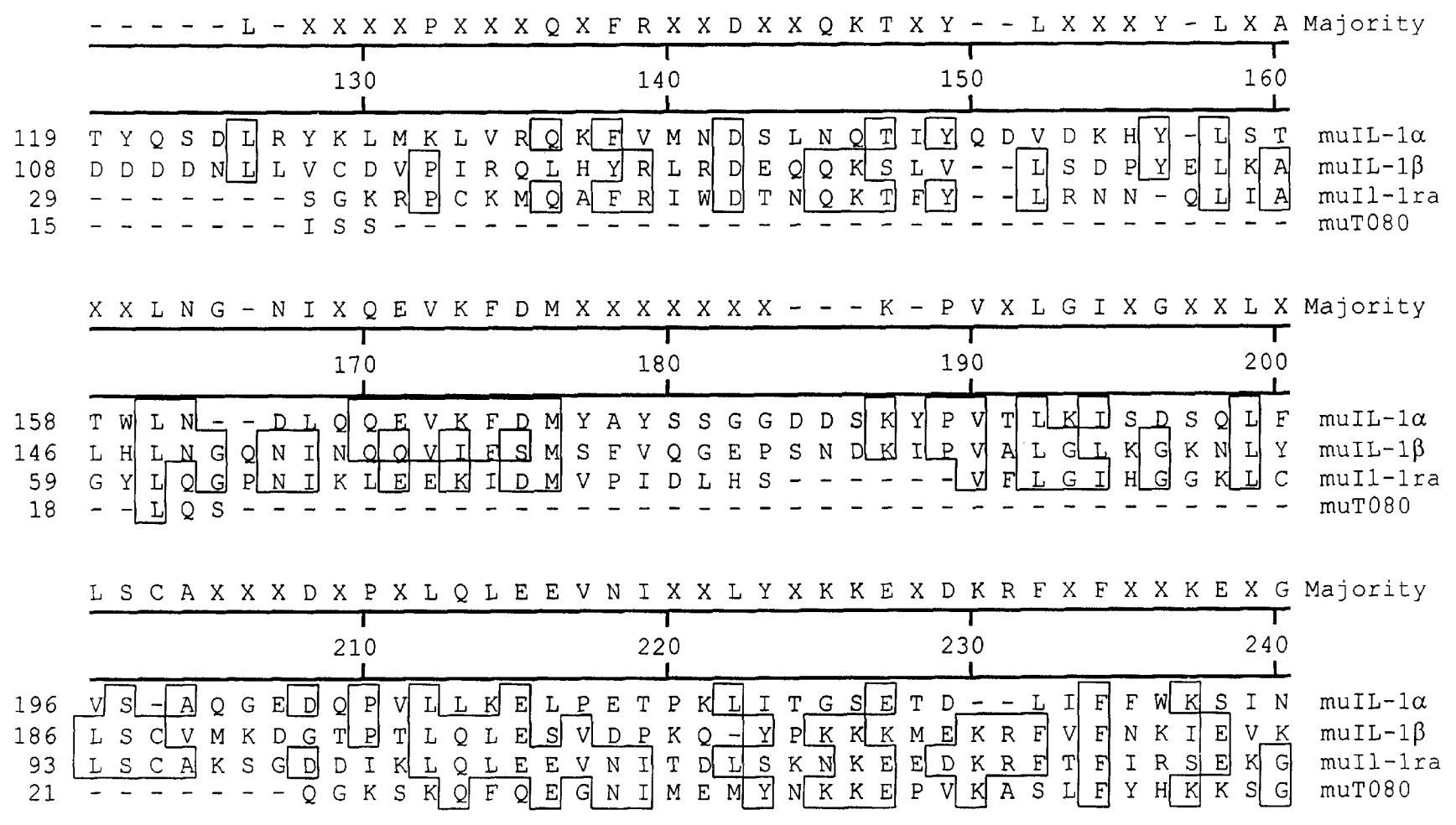
Figure 3C:
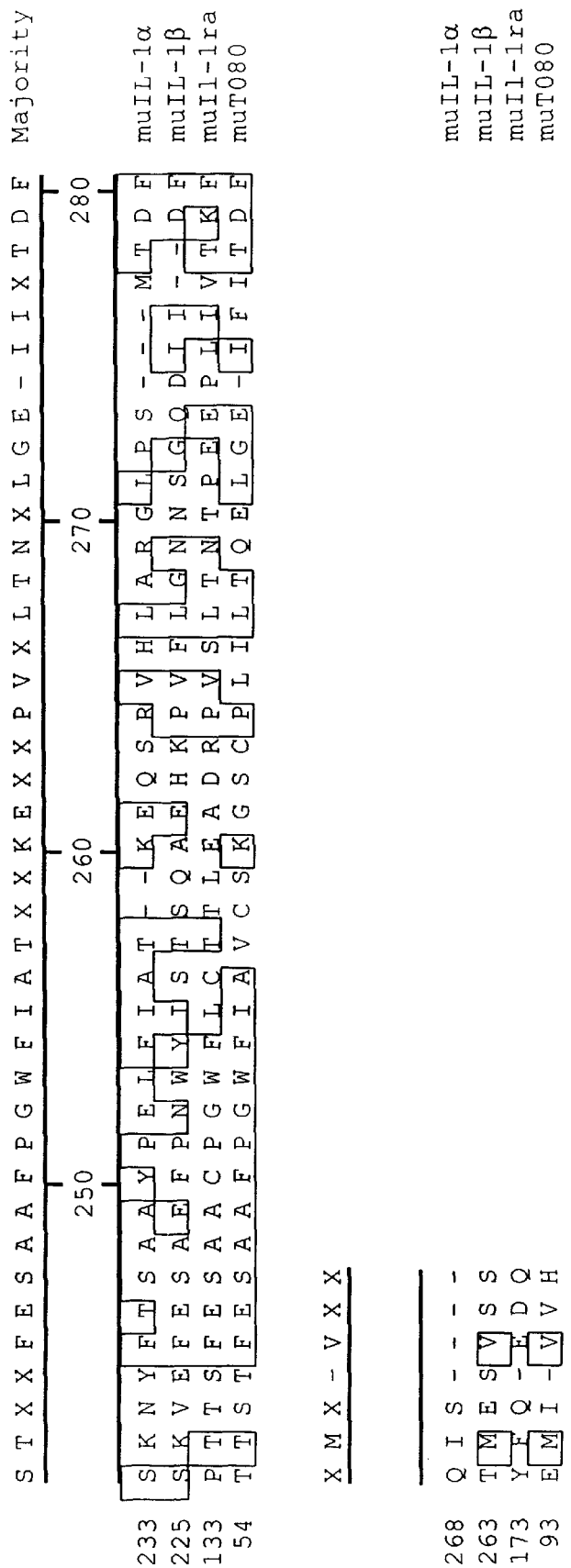

An alignment of the amino acid sequences of murine SPOIL-1 with murine IL-1ra (Swiss-Prot™ Accession No. P25085), as well as murine IL-1α (Swiss-Prot™ Accession No. P01582) and murine IL-1β (Swiss-Prot™ Accession No. P10749) is shown in FIG. 3. (The alignment was generated using MegAlign™ sequence alignment software). The initial pairwise alignment step was performed using a Wilbur-Lipmann algorithm with a K-tuple of 1, a GAP penalty of 3, a window of 5, and diagonals saved set to =5. The multiple alignment step was performed using the Clustal algorithm with a PAM 250 residue weight Table, a GAP penalty of 10, and a GAP length penalty of 10.)

The entire amino acid sequence of SEQ ID NO:2 was subcloned into retroviral vector MSCVneo (Hawley, et al. (1994) *Gene Therapy* 1:136–138) and used for retroviral delivery. Bone marrow infected with the retroviral vector expressing SPOIL-1 was transplanted into irradiated mice recipients. Bones removed from these mouse recipients, histologically, appeared thicker than the bones of control mice. In addition, spleen cells (i.e., a source of osteoclast progenitors) which were removed from mice recipients and were cultured on a bone marrow cell line, demonstrated reduced osteoclast production than the spleen cells of control mice. These experiments are discussed in further detail herein.

Various aspects of the invention are described in further detail in the following subsections:

I. Isolated Nucleic Acid Molecules

One aspect of the invention pertains to isolated nucleic acid molecules that encode SPOIL-1 proteins or biologically active portions thereof, as well as nucleic acid fragments sufficient for use as hybridization probes to identify SPOIL-1-encoding nucleic acids (e.g., SPOIL-1 mRNA) and fragments for use as PCR primers for the amplification or mutation of SPOIL-1 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated SPOIL-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:4, or a portion thereof, can be isolated using standard molecular biology techniques and the sequence information provided herein. Using all or portion of the nucleic acid sequence of SEQ ID NO:1, SEQ ID NO:3 or SEQ ID NO:4 as a hybridization probe, SPOIL-1 nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed, Cold Spring Harbor Laboratory, Cold Spring Harbor Laboratory Press, Cold Spring Harbor, N.Y., 1989). In another embodiment, a portion of the nucleic acid sequence of SEQ ID NO:1, from nucleotide 1 to 15 or 447 to 667, can used as a hybridization probe.

Moreover, a nucleic acid molecule encompassing all or a portion of SEQ ID NO:1, SEQ ID NO:3 or SEQ ID NO:4 can be isolated by the polymerase chain reaction (PCR) using synthetic oligonucleotide primers designed based upon the sequence of SEQ ID NO:1, SEQ ID NO:3 or SEQ ID NO:4.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to SPOIL-1 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:3. The sequence of SEQ ID NO:3 corresponds to murine SPOIL-1 cDNA. This cDNA comprises sequences encoding the murine SPOIL-1 protein (i.e., "the coding region", from nucleotides 135–431 of SEQ ID NO:1).

In another preferred embodiment, an isolated nucleic acid molecule of the invention comprises the nucleotide sequence shown in SEQ ID NO:4. The sequence of SEQ ID NO:4 corresponds to murine SPOIL-1 cDNA. This cDNA comprises sequences encoding the mature SPOIL-1 protein (i.e., from nucleotides 186–431 of SEQ ID NO:1 after the signal sequence has been cleaved).

In yet another embodiment, an isolated nucleic acid molecule of the invention comprises the nucleotide sequence shown in SEQ ID NO:1. The sequence of SEQ ID NO:1 corresponds coding and noncoding regions of murine SPOIL-1 cDNA. This cDNA comprises sequences encoding the murine SPOIL-1 protein (i.e., "the coding region", from nucleotides 135–431) and noncoding regions (i.e., from nucleotides 1–134 and from nucleotides 432–746).

In another preferred embodiment, an isolated nucleic acid molecule of the invention comprises a nucleic acid molecule which is a complement of the nucleotide sequence shown in SEQ ID NO:1, SEQ ID NO:3, SEQ ID NO:4, or a portion of any of these nucleotide sequences. A nucleic acid molecule which is complementary to the nucleotide sequence shown in SEQ ID NO:1, SEQ ID NO:3 or SEQ ID NO:4, is one which is sufficiently complementary to the nucleotide sequence shown in SEQ ID NO:1, SEQ ID NO:3 or SEQ ID NO:4 such that it can hybridize to the nucleotide sequence shown in SEQ ID NO:1, SEQ ID NO:3 or SEQ ID NO:4, thereby forming a stable duplex.

In still another preferred embodiment, an isolated nucleic acid molecule of the present invention comprises a nucleotide sequence which is at least about 60–65%, preferably at least about 70–75%, more preferable at least about 80–85%, and even more preferably at least about 90–95% or more homologous to the nucleotide sequences shown in SEQ ID NO:1, SEQ ID NO:3 or SEQ ID NO:4, or a portion of any of these nucleotide sequences.

Moreover, the nucleic acid molecule of the invention can comprise only a portion of the nucleic acid sequence of SEQ ID NO:1, SEQ ID NO:3 or SEQ ID NO:4, for example a fragment which can be used as a probe or primer or a fragment encoding a biologically active portion of a SPOIL-1 protein. The nucleotide sequence determined from the cloning of the murine SPOIL-1 genes allows for the generation of probes and primers designed for use in identifying and/or cloning SPOIL-1 homologues in other cell types, e.g., from other tissues, as well as SPOIL-1 homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of a sense sequence of SEQ ID NO:1, SEQ ID NO:3 or SEQ ID NO:4 of an anti-sense sequence of SEQ ID NO:1, SEQ ID NO:3 or SEQ ID NO:4 or of a naturally occurring mutant of SEQ ID NO:1, SEQ ID NO:3, SEQ ID NO:4. In an exemplary embodiment, a nucleic acid molecule of the present invention comprises a nucleotide sequence which hybridizes under stringent hybridization conditions to a nucleic acid molecule comprising the nucleotide sequence of SEQ ID NO:1, SEQ ID NO:3 or SEQ ID NO:4.

Probes based on the murine SPOIL-1 nucleotide sequence can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a SPOIL-1 protein, such as by measuring a level of a SPOIL-1-encoding nucleic acid in a sample of cells from a subject e.g., detecting SPOIL-1 mRNA levels or determining whether a genomic SPOIL-1 gene has been mutated or deleted.

A nucleic acid fragment encoding a "biologically active portion of a SPOIL-1 protein" can be prepared by isolating a portion of SEQ ID NO:1, SEQ ID NO:3 or SEQ ID NO:4, which encodes a polypeptide having a SPOIL-1 biological activity (the biological activities of the SPOIL-1 proteins have previously been described), expressing the encoded portion of the SPOIL-1 protein (e.g., by recombinant expression in vitro) and assessing the activity of the encoded portion of the SPOIL-1 protein.

The invention further encompasses nucleic acid molecules that differ from the nucleotide sequence shown in SEQ ID NO:1, SEQ ID NO:3 or SEQ ID NO:4 due to degeneracy of the genetic code and thus encode the same SPOIL-1 proteins as those encoded by the nucleotide sequence shown in SEQ ID NO:1, SEQ ID NO:3 or SEQ ID NO:4. In another embodiment, an isolated nucleic acid molecule of the invention has a nucleotide sequence encoding a protein having an amino acid sequence shown in SEQ ID NO:2 or SEQ ID NO:5.

In addition to the murine SPOIL-1 nucleotide sequences shown in SEQ ID NO:1, SEQ ID NO:3 or SEQ ID NO:4, it will be appreciated by those skilled in the art that DNA sequence polymorphisms that lead to changes in the amino acid sequences of the SPOIL-1 proteins may exist within a population (e.g., the mouse population). Such genetic polymorphism in the SPOIL-1 genes may exist among individuals within a population due to natural allelic variation. As used herein, the terms "gene" and "recombinant gene" refer to nucleic acid molecules comprising an open reading frame encoding a SPOIL-1 protein, preferably a mammalian SPOIL-1 protein. Such natural alletic variations can typically result in 1–5% variance in the nucleotide sequence of a SPOIL-1 gene. Any and all such nucleotide variations and resulting amino acid polymorphisms in SPOIL-1 genes that are the result of natural allelic variation and that do not alter the functional activity of a SPOIL-1 protein are intended to be within the scope of the invention.

Moreover, nucleic acid molecules encoding SPOIL-1 proteins from other species, and thus which have a nucleotide sequence which differs from the murine sequence of SEQ ID NO: 1, SEQ ID NO:3 or SEQ ID NO:4 are intended to be within the scope of the invention. Nucleic acid molecules corresponding to natural allelic variants and homologues of the SPOIL-1 cDNAs of the invention can be isolated based on their homology to the murine SPOIL-1 nucleic acids disclosed herein using the murine cDNA, or a portion thereof, as a hybridization probe according to standard hybridization techniques under stringent hybridization conditions.

Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1, SEQ ID NO:3 or SEQ ID NO:4. In other embodiment, the nucleic acid is at least 30, 50, 100, 250 or 500 nucleotides in length. As used herein, the term "hybridizes under stringent conditions" is intended to describe conditions for hybridization and washing under which nucleotide sequences at least 65% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6X sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1, SEQ ID NO: 3 or SEQ ID NO:4 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the SPOIL-1 sequences that may exist in the population, the skilled artisan will further appreciate that changes can be introduced by mutation into the nucleotide sequences of SEQ ID NO:1, SEQ ID NO:3 or SEQ ID NO:4, thereby leading to changes in the amino acid sequence of the encoded SPOIL-1 proteins, without altering the functional ability of the SPOIL-1 proteins. For example, nucleotide substitutions leading to amino acid substitutions at "nonessential" amino acid residues can be made in the sequence of SEQ ID NO:1, SEQ ID NO:3 or SEQ ID NO:4. A "non-essential" amino acid residue is a residue that can be altered from the wild-type sequence of SPOIL-1 (e.g., the sequence of SEQ ID NO:2 or SEQ ID NO:5) without altering the biological activity, whereas an "essential" amino acid residue is required for biological activity. For example, amino acid residues that are conserved among the SPOIL-1 proteins of the present invention, are predicted to be particularly unamenable to alteration. Furthermore, amino acid residues that are conserved between SPOIL-1 protein and other IL-1ra proteins are not likely to be amenable to alteration.

Accordingly, another aspect of the invention pertains to nucleic acid molecules encoding SPOIL-1 proteins that contain changes in amino acid residues that are not essential for activity. Such SPOIL-1 proteins differ in amino acid sequence from SEQ ID NO:2 or SEQ ID NO:5 yet retain biological activity. In one embodiment, the isolated nucleic acid molecule comprises a nucleotide sequence encoding a protein, wherein the protein comprises an amino acid sequence at least about 60% homologous to the amino acid sequence of SEQ ID NO:2 or SEQ ID NO:5. Preferably, the protein encoded by the nucleic acid molecule is at least about 65–70% homologous to SEQ ID NO:2 or SEQ ID NO:5, more preferably at least about 75–80% homologous to SEQ ID NO:2 or SEQ ID NO:5, even more preferably at least about 85–90% homologous to SEQ ID NO:2 or SEQ ID NO:5, and most preferably at least about 95% homologous to SEQ ID NO:2 or SEQ ID NO:5.

An isolated nucleic acid molecule encoding a SPOIL-1 protein homologous to the protein of SEQ ID NO:2 or SEQ ID NO:5 can be created by introducing one or more nucleotide substitutions, additions or deletions into the nucleotide sequence of SEQ ID NO:1, SEQ ID NO:3 or SEQ ID NO:4, such that one or more amino acid substitutions, additions or deletions are introduced into the encoded protein. Mutations can be introduced into SEQ ID NO:1, SEQ ID NO:3 or SEQ ID NO:4 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a SPOIL-1 protein is preferably replaced with another amino acid residue from the same side chain family. Alternatively, in another embodiment, mutations can be introduced randomly along all or part of a SPOIL-1 coding sequence, such as by saturation mutagenesis, and the resultant mutants can be screened for SPOIL-1 biological activity to identify mutants that retain activity. Following mutagenesis of SEQ ID NO:1, SEQ ID NO:3 or SEQ ID NO:4, the encoded protein can be expressed recombinantly and the activity of the protein can be determined.

In a preferred embodiment, a mutant SPOIL-1 protein can be assayed for (1) the ability to modulate IL-1 signal transduction, either in vitro or in vivo; (2) modulate IL-1 stimulated cell development or differentiation, either in vitro or in vivo; and (3) modulate IL-1 stimulated cellular proliferation, either in vitro or in vivo.

In addition to the nucleic acid molecules encoding SPOIL-1 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire SPOIL-1 coding strand, or to only a portion thereof. In one embodiment, an antisense nucleic acid molecule is antisense to a "coding region" of the coding strand of a nucleotide sequence encoding SPOIL-1. The term "coding region" refers to the region of the nucleotide sequence comprising codons which are translated into amino acid residues (e.g., amino acid residues 1–98 of SEQ ID NO:3 or amino acid residues 1–81 of SEQ ID NO:4).

Given the coding strand sequences encoding SPOIL-1 disclosed herein (e.g., SEQ ID NO:1, SEQ ID NO:3, SEQ ID NO:4), antisense nucleic acids of the invention can be designed according to the rules of Watson and Crick base pairing. The antisense nucleic acid molecule can be complementary to the entire coding region of SPOIL-1 mRNA, but more preferably is an oligonucleotide which is antisense to only a portion of the coding region of SPOIL-1 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a SPOIL-1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave SPOIL-1 mRNA transcripts to thereby inhibit translation of SPOIL-1 mRNA. A ribozyme having specificity for a SPOIL-1-encoding nucleic acid can be designed based upon the nucleotide sequence of a SPOIL-1 cDNA disclosed herein (i.e., SEQ ID NO:1, SEQ ID NO:3 or SEQ ID NO:4). For example, a derivative of a Tetrahymena L-19 IVS RNA can be constructed in which the nucleotide sequence of the active site is complementary to the nucleotide sequence to be cleaved in a SPOIL-1-encoding mRNA. See, e.g., Cech et al. U.S. Pat. No. 4,987,071; and Cech et al. U.S. Pat. No. 5,116,742. Alternatively, SPOIL-1 mRNA can be used to select a catalytic RNA having a specific ribonuclease activity from a pool of RNA molecules. See, e.g., Bartel, D. and Szostak, J. W. (1993) *Science* 261:1411–1418.

Alternatively, SPOIL-1 gene expression can be inhibited by targeting nucleotide sequences complementary to the regulatory region of the SPOIL-1 (e.g., the SPOIL-1 promoter and/or enhancers) to form triple helical structures that prevent transcription of the SPOIL-1 gene in target cells. See generally, Helene, C. (199 1) *Anticancer Drug Des.* 6(6) :569–84; Helene, C. et al. (1992) *Ann. N.Y. Acad. Sci.* 660:27–36; and Maher, L. J. (1992) *Bioassays* 14(12) :807–15.

In yet another embodiment, the SPOIL-1 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. PNAS 93: 14670–675.

PNAs of SPOIL-1 nucleic acid molecules can be used therapeutic and diagnostic applications. For example, PNAs can be used as antisense or antigene agents for sequence-specific modulation of gene expression by, for example, inducing transcription or translation arrest or inhibiting replication. PNAs of SPOIL-1 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of SPOIL-1 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of SPOIL-1 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). the synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric moleclues can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553–6556; Lemaitre et al. (1987) *Proc. Natl. Acad. Sci. USA* 84:648–652; PCT Publication No. WO88/09810, published Dec. 15, 1988) or the blood-brain barrier (see, e.g., PCT Publication No. WO89/10134, published Apr. 25, 1988). In addition, oligonucleotides can be modified with hybridization-triggered cleavage agents (See, e.g., Krol et al. (1988) *BioTechniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated SPOIL-1 Proteins and Anti-SPOIL-1 Antibodies

One aspect of the invention pertains to isolated SPOIL-1 proteins, and biologically active portions thereof, as well as polypeptide fragments suitable for use as immunogens to raise anti-SPOIL-1 antibodies. In one embodiment, native SPOIL-1 proteins can be isolated from cells or tissue sources by an appropriate purification scheme using standard protein purification techniques. In another embodiment, SPOIL-1 proteins are produced by recombinant DNA techniques. Alternative to recombinant expression, a SPOIL-1 protein or polypeptide can be synthesized chemically using standard peptide synthesis techniques.

An "isolated" or "purified" protein or biologically active portion thereof is substantially free of cellular material or other contaminating proteins from the cell or tissue source from which the SPOIL-1 protein is derived, or substantially free from chemical precursors or other chemicals when chemically synthesized. The language "substantially free of cellular material" includes preparations of SPOIL-1 protein in which the protein is separated from cellular components of the cells from which it is isolated or recombinantly produced. In one embodiment, the language "substantially free of cellular material" includes preparations of SPOIL-1 protein having less than about 30% (by dry weight) of non-SPOIL-1 protein (also referred to herein as a "contaminating protein"), more preferably less than about 20% of non-SPOIL-1 protein, still more preferably less than about 10% of non-SPOIL-1 protein, and most preferably less than about 5% non-SPOIL-1 protein. When the SPOIL-1 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of SPOIL-1 protein in which the protein is separated from chemical precursors or other chemicals which are involved in the synthesis of the protein. In one embodiment, the language "substantially free of chemical precursors or other chemicals" includes preparations of SPOIL-1 protein having less than about 30% (by dry weight) of chemical precursors or non-SPOIL-1 chemicals, more preferably less than about 20% chemical precursors or non-SPOIL-1 chemicals, still more preferably less than about 10% chemical precursors or non-SPOIL-1 chemicals, and most preferably less than about 5% chemical precursors or non-SPOIL-1 chemicals.

Biologically active portions of a SPOIL-1 protein include peptides comprising 30 amino acid sequences sufficiently homologous to or derived from the amino acid sequence of the SPOIL-1 protein, e.g., the amino acid sequence shown in SEQ ID NO:2, which include less amino acids than the full length SPOIL-1 proteins, and exhibit at least one activity of a SPOIL-1 protein. Typically, biologically active portions comprise a domain or motif with at least one activity of the SPOIL-1 protein. A biologically active portion of a SPOIL-1 protein can be a polypeptide which is, for example, 10, 25, 50, 100 or more amino acids in length.

In one embodiment, a biologically active portion of a SPOIL-1 protein comprises at least an IL-1 signature domain. In yet another embodiment, a biologically active portion of a SPOIL-1 protein comprises at least a signal sequence. In yet another embodiment, a biologically active portion of a SPOIL-1 protein comprises and IL-1 signature domain and a signal sequence.

In an alternative embodiment, a biologically active portion of a SPOIL-1 protein comprises a SPOIL-1 amino acid sequence lacking an IL-1 signature domain. In yet another embodiment, a biologically active portion of a SPOIL-1 protein comprises a SPOIL-1 amino acid sequence lacking a signal sequence.

It is to be understood that a preferred biologically active portion of a SPOIL-1 protein of the present invention may contain at least one of the above-identified structural domains. Another preferred biologically active portion of a SPOIL-1 protein may contain at least two of the above-identified structural domains. Another preferred biologically active portion of an EDIRF protein may contain at least three or more of the above-identified structural domains.

Moreover, other biologically active portions, in which other regions of the protein are deleted, can be prepared by recombinant techniques and evaluated for one or more of the functional activities of a native SPOIL-1 protein.

In a preferred embodiment, the SPOIL-1 protein has an amino acid sequence shown in SEQ ID NO:2 or SEQ ID NO:5. In other embodiments, the SPOIL-1 protein is substantially homologous to SEQ ID NO:2 or SEQ ID NO:5 and retains the functional activity of the protein of SEQ ID NO:2 or SEQ ID NO:5 yet differs in amino acid sequence due to natural allelic variation or mutagenesis, as described in detail in subsection 1 above. Accordingly, in another embodiment, the SPOIL-1 protein is a protein which comprises an amino acid sequence at least about 60% homologous to the amino acid sequence of SEQ ID NO:2 or SEQ ID NO:5 and, preferably, retains a functional activity of the SPOIL-1 proteins of SEQ ID NO:2 or SEQ ID NO:5. Preferably, the protein is at least about 70% homologous to SEQ ID NO:2 or SEQ ID NO:5, more preferably at least about 80% homologous to SEQ ID NO:2 or SEQ ID NO:5, even more preferably at least about 90% homologous to SEQ ID NO:2 or SEQ ID NO:5, and most preferably at least about 95% or more homologous to SEQ ID NO:2 or SEQ ID NO:5.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the SPOIL-1 amino acid sequence of SEQ ID NO:2, having 86 amino acid residues, at least 66, preferably at least 46, more preferably at least 26 are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions× 100).

The comparison of sequences and determination of percent homology between two sequences can be accomplished using a mathematical algorithim. A preferred, non-limiting example of a mathematical algorithim utilized for the comparison of sequences is the algorithm of Karlin and Altschul (1990) Proc. Natl. Acad. Sci. USA 87:2264–68, modified as in Karlin and Altschul (1993) Proc. Natl. Acad. Sci. USA 90:5873–77. Such an algorithm is incorporated into the NBLAST and XBLAST programs (version 2.0) of Altschul, et al. (1990) J. Mol. Biol. 215:403–10. BLAST nucleotide searches can be performed performed with the NBLAST program, score=100, wordlength=12 to obtain nucleotide sequences homologous to SPOIL-1 nucleic acid molecules of the invention. BLAST protein searches can be performed with the XBIAST program, score=50, wordlength=3 to obtain amino acid sequences homologous to TAP-1 protein molecules of the invention. To obtain gapped alignments for comparison purposes, Gapped BLAST can be utilized as described in Altschul et al., (1997) Nucleic Acids Research 25(17):3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithim utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The invention also provides SPOIL-1 chimeric or fusion proteins. As used herein, a SPOIL-1 "chimeric protein" or "fusion protein" comprises a SPOIL-1 polypeptide operatively linked to a non-SPOIL-1 polypeptide. A "SPOIL-1 polypeptide" refers to a polypeptide having an amino acid sequence corresponding to SPOIL-1, whereas a "non-SPOIL-1 polypeptide" refers to a polypeptide having an amino acid sequence corresponding to a protein which is not substantially homologous to the SPOIL-1 protein, e.g., a protein which is different from the SPOIL-1 protein and which is derived from the same or a different organism. Within a SPOIL-1 fusion protein the SPOIL-1 polypeptide can correspond to all or a portion of a SPOIL-1 protein. In a preferred embodiment, a SPOIL-1 fusion protein comprises at least one biologically active portion of a SPOIL-1 protein. Within the fusion protein, the term "operatively linked" is intended to indicate that the SPOIL-1 polypeptide and the non-SPOIL-1 polypeptide are fused in-frame to each other. The non-SPOIL-1 polypeptide can be fused to the N-terminus or C-terminus of the SPOIL-1 polypeptide.

In yet another embodiment, the fusion protein is a GST-SPOIL-1 fusion protein in which the SPOIL-1 sequences are fused to the C-terminus of the GST sequences. Such fusion proteins can facilitate the purification of recombinant SPOIL-1.

In another embodiment, the fusion protein is a SPOIL-1 protein containing a heterologous signal sequence at its N-terminus. For example, the native SPOIL-1 signal sequence (i.e, about amino acids 1 to 17 of SEQ ID NO:2) can be removed and replaced with a signal sequence from another protein. In certain host cells (e.g., mammalian host cells), expression and/or secretion of SPOIL-1 can be increased through use of a heterologous signal sequence.

In yet another embodiment, the fusion protein is a SPOIL-1-immunoglobulin fusion protein in which the SPOIL-1 sequence are fused to sequences derived from a member of the immunoglobulin protein family. Soluble derivatives have also been made of cell surface glycoproteins in the immunoglobulin gene superfamily consisting of an extracellular domain of the cell surface glycoprotein fused to an immunoglobulin constant (Fc) region (see e.g., Capon, D. J. et al. (1989) Nature 337:525–531 and Capon U.S. Pat. Nos. 5,116,964 and 5,428,130 [CD4-IgG1 constructs]; Linsley, P. S. et al. (1991) J. Exp. Med. 173:721–730 [a CD28-IgG1 construct and a B7-1-IgG1 construct]; and Linsley, P. S. etal. (1991) J. Exp. Med. 174:561–569 and U.S. Pat. No. 5,434, 131[a CTLA4-IgG1]). Such fusion proteins have proven useful for modulating receptor-ligand interactions. Soluble derivatives of cell surface proteins of the tumor necrosis factor receptor (TNFR) superfamily proteins have been made consisting of an extracellular domain of the cell surface receptor fused to an immunoglobulin constant (Fc) region (See for example Moreland et al. (1997) N. Engl. J. Med. 337(3):141–147; van der Poll et al. (1 997) Blood 89(10):3727–3734; and Ammann et al. (1997) J. Clin. Invest. 99(7):1699–1703. )

The SPOIL-1-immunoglobulin fusion proteins of the invention can be incorporated into pharmaceutical compositions and administered to a subject to inhibit an interaction between a SPOIL-1 protein and a SPOIL-1 target molecule on the surface of a cell, to thereby suppress SPOIL-1-mediated signal transduction in vivo. The SPOIL-1-immunoglobulin fusion proteins can be used to affect the bioavailability of a SPOIL-1 cognate ligand. Inhibition of the SPOIL-1 ligand/SPOIL-1 interaction may be useful therapeutically for both the treatment of inflammation and immune disorders, as well as modulating (e.g., promoting or inhibiting) immune cell responses, cell adhesion, and/or cell homing. Moreover, the SPOIL-1-immunoglobulin fusion proteins of the invention can be used as immunogens to produce anti-SPOIL-1 antibodies in a subject, to purify SPOIL-1 ligands and in screening assays to identify molecules which inhibit the interaction of SPOIL-1 with a SPOIL-1 target molecule.

Preferably, a SPOIL-1 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A SPOIL-1-encoding nucleic acid can be cloned into such an expression vector such that the fusion moiety is linked in-frame to the SPOIL-1 protein.

The present invention also pertains to variants of the SPOIL-1 proteins which function as SPOIL-1-IL-1 agonists (mimetics). Variants of the SPOIL-1 protein can be generated by mutagenesis, e.g., discrete point mutation or truncation of the SPOIL-1 protein. A SPOIL-1 agonist of IL-1 can retain substantially the same, or a subset, of the biological activities of the naturally occurring form of the SPOIL-1 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the SPOIL-1 proteins.

In one embodiment, a SPOIL-1 protein which acts as an IL-1 receptor antagonist can be converted into an IL-1 agonist by site specific mutagenesis. For example, the aspartic acid at amino acid residue 91 of SEQ ID NO:2 or amino acid residue 74 of SEQ ID NO:5, can be substituted with a lysine to create an IL-1 agonist. Similar methods of converting IL-1ra into an IL-1 agonist are set forth in Ju et al. (1991) *Proc. Natl. Acad. Sci. USA* 88:2658–2662.

In another embodiment, variants of the SPOIL-1 protein which function as SPOIL-1-IL-1 receptor agonists (mimetics) can be identified by screening combinatorial libraries of mutants, e.g., truncation mutants, of the SPOIL-1 protein for SPOIL-1 protein IL-1 agonist. In one embodiment, a variegated library of SPOIL-1 variants is generated by combinatorial mutagenesis at the nucleic acid level and is encoded by a variegated gene library. A variegated library of SPOIL-1 variants can be produced by, for example, enzymatically ligating a mixture of synthetic oligonucleotides into gene sequences such that a degenerate set of potential SPOIL-1 sequences is expressible as individual polypeptides, or alternatively, as a set of larger fusion proteins (e.g., for phage display) containing the set of SPOIL-1 sequences therein. There are a variety of methods which can be used to produce libraries of potential SPOIL-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential SPOIL-1 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the SPOIL-1 protein coding sequence can be used to generate a variegated population of SPOIL-1 fragments for screening and subsequent selection of variants of a SPOIL-1 protein. In one embodiment, a library of coding sequence fragments can be generated by treating a double stranded PCR fragment of a SPOIL-1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the SPOIL-1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of SPOIL-1 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify SPOIL-1 variants (Arkin and Yourvan (1 992) *PNAS* 89:7811–7815; Delgrave et al. (1993) Protein Engineering 6(3):327–33 1).

In one embodiment, cell based assays can be exploited to analyze a variegated SPOIL-1 library. For example, a library of expression vectors can be transfected into a cell line which ordinarily responds to a particular ligand in a SPOIL-1-dependent manner. The transfected cells are then contacted with the ligand and the effect of expression of the mutant on signaling by the ligand can be detected, e.g., by measuring any of a number of immune cell responses. Plasmid DNA can then be recovered from the cells which score for inhibition, or alternatively, potentiation of ligand induction, and the individual clones further characterized.

An isolated SPOIL-1 protein, or a portion or fragment thereof, can be used as an immunogen to generate antibodies that bind SPOIL-1 using standard techniques for polyclonal and monoclonal antibody preparation. The full-length SPOIL-1 protein can be used or, alternatively, the invention provides antigenic peptide fragments of SPOIL-1 for use as immunogens. The antigenic peptide of SPOIL-1 comprises at least 8 amino acid residues of the amino acid sequence shown in SEQ ID NO:2 or SEQ ID NO:5 and encompasses an epitope of SPOIL-1 such that an antibody raised against the peptide forms a specific immune complex with SPOIL-1. Preferably, the antigenic peptide comprises at least 10 amino acid residues, more preferably at least 15 amino acid residues, even more preferably at least 20 amino acid residues, and most preferably at least 30 amino acid residues.

A SPOIL-1 immunogen typically is used to prepare antibodies by immunizing a suitable subject, (e.g., rabbit, goat, mouse or other mammal) with the immunogen. An appropriate immunogenic preparation can contain, for example, recombinantly expressed SPOIL-1 protein or a chemically synthesized SPOIL-1 polypeptide. The preparation can further include an adjuvant, such as Freund's complete or incomplete adjuvant, or similar immunostimulatory agent. Immunization of a suitable subject with an immunogenic SPOIL-1 preparation induces a polyclonal anti-SPOIL-1 antibody response.

Accordingly, another aspect of the invention pertains to anti-SPOIL-1 antibodies. The term "antibody" as used herein refers to immunoglobulin molecules and immunologically active portions of immunoglobulin molecules, i.e., molecules that contain an antigen binding site which specifically binds (immunoreacts with) an antigen, such as SPOIL-1. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind SPOIL-1. The term "monoclonal antibody" or "monoclonal antibody composition", as used herein, refers to a population of antibody molecules that contain only one species of an antigen binding site capable of immunoreacting with a particular epitope of SPOIL-1. A monoclonal antibody composition thus typically displays a single binding affinity for a particular SPOIL-1 protein with which it immunoreacts.

Polyclonal anti-SPOIL-1 antibodies can be prepared as described above by immunizing a suitable subject with a SPOIL-1 immunogen. The anti-SPOIL-1 antibody titer in the immunized subject can be monitored over time by standard techniques, such as with an enzyme linked immunosorbent assay (ELISA) using immobilized SPOIL-1. If desired, the antibody molecules directed against SPOIL-1 can be isolated from the mammal (e.g., from the blood) and further purified by well known techniques, such as protein A chromatography to obtain the IgG fraction. At an appropriate time after immunization, e.g., when the anti-SPOIL-1 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (I981) *J. Immunol.* 127:539–46; Brown et al. (1980) *J. Biol. Chem.* 255:4980–83; Yeh et al. (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a SPOIL-1 immunogen as described above, and the culture supernatants of the resulting hybridoma cells are screened to identify a hybridoma producing a monoclonal antibody that binds SPOIL-1.

Any of the many well known protocols used for fusing lymphocytes and immortalized cell lines can be applied for the purpose of generating an anti-SPOIL-1 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion arc then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind SPOIL-1, e.g., using a standard ELISA assay.

Alternative to preparing monoclonal antibody-secreting hybridomas, a monoclonal anti-SPOIL-1 antibody can be identified and isolated by screening a recombinant combinatorial immunoglobulin library (e.g., an antibody phage display library) with SPOIL-1 to thereby isolate immunoglobulin library members that bind SPOIL-1. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc. Acid Res.* 19:4133–4137; Barbas et al. (1991) *PNAS* 88:7978–7982; and McCafferty et al. *Nature* (1990) 348:552–55.

Additionally, recombinant anti-SPOIL-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173, 494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Nati. Cancer Inst.* 80:1553–1559); Morrison, S. L. (1985) *Science*

229:1202–1207; Oi et al. (1986) *BioTechniques* 4:214; Winter U.S. Pat. No. 5,225,539; Jones et al. (1 986) *Nature* 321:552–525; Verhoeyan et al. (1988) *Science* 239:1534; and Bcidler et al. (1988) *J. Immunol.* 141:4053–4060.

An anti-SPOIL-1 antibody (e.g., monoclonal antibody) can be used to isolate SPOIL-1 by standard techniques, such as affinity chromatography or immunoprecipitation. An anti-SPOIL-1 antibody can facilitate the purification of natural SPOIL-1 from cells and of recombinantly produced SPOIL-1 expressed in host cells. Moreover, an anti-SPOIL-1 antibody can be used to detect SPOIL-1 protein (e.g., in a cellular lysate or cell supernatant) in order to evaluate the abundance and pattern of expression of the SPOIL-1 protein. Anti-SPOIL-1 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

III. Recombinant Expression Vectors and Host Cells

Another aspect of the invention pertains to vectors, preferably expression vectors, containing a nucleic acid encoding SPOIL-1 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., SPOIL-1 proteins, mutant forms of SPOIL-1, fusion proteins, etc.).

The recombinant expression vectors of the invention can be designed for expression of SPOIL-1 in prokaryotic or eukaryotic cells. For example, SPOIL-1 can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1 990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in SPOIL-1 activity assays, in SPOIL-1 ligand binding (e.g., direct assays or competitive assays described in detail below), to generate antibodies specific for SPOIL-1 proteins, as examples. In a preferred embodiment, a SPOIL-1 fusion expressed in a retroviral expression vector of the present invention can be utilized to infect bone marrow cells which are subsequently transplanted into irradiated recipients. The pathology of the subject recipient is then examined after sufficient time has passed (e.g five (5) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11 d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the SPOIL-1 expression vector is a yeast expression vector. Examples of vectors for expression in yeast S. cerivisae include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (Invitrogen Corp, San Diego, Calif.).

Alternatively, SPOIL-1 can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43 :235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to SPOIL-1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, SPOIL-1 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding SPOIL-1 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) SPOIL-1 protein. Accordingly, the invention further provides methods for producing SPOIL-1 protein using the host cells of the invention. In one embodiment, the method comprises culturing the host cell of invention (into which a recombinant expression vector encoding SPOIL-1 has been introduced) in a suitable medium such that SPOIL-1 protein is produced. In another embodiment, the method further comprises isolating SPOIL-1 from the medium or the host cell.

The host cells of the invention can also be used to produce nonhuman transgenic animals. For example, in one embodiment, a host cell of the invention is a fertilized oocyte or an embryonic stem cell into which SPOIL-1-coding sequences have been introduced. Such host cells can then be used to create non-human transgenic animals in which exogenous SPOIL-1 sequences have been introduced into their genome or homologous recombinant animals in which endogenous SPOIL-1 sequences have been altered. Such animals are useful for studying the function and/or activity of SPOIL-1 and for identifying and/or evaluating modulators of SPOIL-1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transge transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous SPOIL-1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing SPOIL-1-encoding nucleic acid into the male pronuclei of a fertilized oocyte, e.g., by microinjection, retroviral infection, and allowing the oocyte to develop in a pseudopregnant female foster animal. The murine SPOIL-1 cDNA sequence of SEQ ID NO:3 can be introduced as a transgene into the genome of a non-human animal. Alternatively, a human homologue of the murine SPOIL-1 gene can be isolated based on hybridization to the murine SPOIL-1 cDNA (described further in subsection I above) and used as a transgene. Intronic sequences and polyadenylation signals can also be included in the transgene to increase the efficiency of expression of the transgene. A tissue-specific regulatory sequence(s) can be operably linked to the SPOIL-1 transgene to direct expression of SPOIL-1 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the SPOIL-1 transgene in its genome and/or expression of SPOIL-1 mRNA in tissues or cells of the animals. A transgenic founder animal can then be used to breed additional animals carrying the transgene. Moreover, transgenic animals carrying a transgene encoding SPOIL-1 can further be bred to other transgenic animals carrying other transgenes.

To create a homologous recombinant animal, a vector is prepared which contains at least a portion of a SPOIL-1 gene into which a deletion, addition or substitution has been introduced to thereby alter, e.g., functionally disrupt, the SPOIL-1 gene. The SPOIL-1 gene can be a human gene, but more preferably, is a non-human SPOIL-1 gene. For example, a murine SPOIL-1 gene of SEQ ID NO:1 or SEQ ID NO:3 can be used to construct a homologous recombination vector suitable for altering an endogenous SPOIL-1 gene in the mouse genome. In a preferred embodiment, the vector is designed such that, upon homologous recombination, the endogenous SPOIL-1 gene is functionally disrupted (i.e., no longer encodes a functional protein; also referred to as a "knock out" vector). Alternatively, the vector can be designed such that, upon homologous recombination, the endogenous SPOIL-1 gene is mutated or otherwise altered but still encodes functional protein (e.g., the upstream regulatory region can be altered to thereby alter the expression of the endogenous SPOIL-1 protein). In the homologous recombination vector, the altered portion of the SPOIL-1 gene is flanked at its 5' and 3' ends by additional nucleic acid of the SPOIL-1 gene to allow for homologous recombination to occur between the exogenous SPOIL-1 gene carried by the vector and an endogenous SPOIL-1 gene in an embryonic stem cell. The additional flanking SPOIL-1 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced SPOIL-1 gene has homologously recombined with the endogenous SPOIL-1 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system ofSaccharomyces cerevisiae (O'Gorman et al. (1991) *Science* 251:1351–1355. If a cre/loxp recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, 1. et al. (1997) *Nature* 385:810–813. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The recontructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The SPOIL-1 nucleic acid molecules, SPOIL-1 proteins, and anti-SPOIL-1 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a SPOIL-1 protein or anti-SPOIL-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology), c) predictive medicine (e.g., diagnostic assays, prognostic assays, monitoring clinical trials); and d) methods of treatment (e.g., therapeutic and prophylactic methods as well as such methods in the context of pharmacogenomics). As described herein, a SPOIL-1 protein of the invention has one or more of the following activities: (i) inhibition of an IL-1-dependent signal transduction pathway; (ii) modulation of secretion of a non-IL-1 cytokine; (iii) modulation of a proinflammatory cytokine; and (iv) modulation of an IL-1 stimulated cell development or differentiation, and can thus be used in, for example, (1) regulation of inflammation; and (2) control of IL-1 stimulated differentiation or development, either in vitro or in vivo. The isolated nucleic acid molecules of the invention can be used, for example, to express SPOIL-1 protein (e.g., via a recombinant expression vector in a host cell in gene therapy applications), to detect SPOIL-1 mRNA (e.g., in a biological sample) or a genetic alteration in an SPOIL-1 gene, and to modulate IL-1 activity, as described further below. In addition, the SPOIL-1 proteins can be screened which modulate the SPOIL-1 activity as well as to treat disorders characterized by insufficient or excessive production of IL-1 which have decreased or aberrant activity compared to normal IL-1 expression (e.g., inflammatory diseases, e.g., rheumatoid arthritis, sepsis, stroke or diabetes, or IL-1 stimulated differentiative or developmental disorders such as bone metabolism disorders, e.g., osteoporosis, Paget's disease of bone, hypercalcemia of malignancy or osteolytic metastases). Soluble forms of the SPOIL-1 protein can be used to bind IL-1 receptors and influence bioavailability of such a receptors cognate ligand. In addition, the anti-SPOIL-1 antibodies of the invention can be used to detect and isolate SPOIL-1 proteins.

A. Screening Assays

The invention provides a method (also referred to herein as a "screening assay") for identifying modulators, i.e., candidate or test compounds or agents (e.g., peptides, peptidomimetics, small molecules or other drugs) which bind to SPOIL-1 proteins or have a stimulatory or inhibitory effect on, for example, SPOIL-1 expression or SPOIL-1 activity and/or have a stimulatory or inhibitory effect on IL-1 stimulated activities.

In one embodiment, the invention provides assays for screening candidate or test compounds which bind to or modulate the activity of a SPOIL-1 target molecule. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner USP 5,223,409), spores (Ladner USP '409), plasmids (Cull et al. (1992) *Proc Natl Acad Sci USA* 89:1865–1869) or on phage (Scott and Smith (1990) *Science* 249:386–390); (Devlin (1990) *Science* 249:404–406);

(Cwirla et al. (1990) *Proc. Natl. Acad. Sci.* 87:6378–6382); (Felici (1991) *J. Mol. Biol.* 222:301–310); (Ladner supra.).

In one embodiment, the screening assay comprises contacting a cell which expresses a SPOIL-1 receptor on the cell surface with a SPOIL-1 protein or biologically-active portion thereof, to form an assay mixture, contacting the assay mixture with a test compound, and determining the ability of the test compound to interact with a SPOIL-1 receptor, wherein determining the ability of the test compound to interact with a SPOIL-1 receptor comprises determining the ability of the test compound to preferentially bind to the SPOIL-1 receptor as compared to the ability of SPOIL-1, or a biologically active portion thereof, to bind to the receptor. In addition, the screening assay can also comprise contacting a cell which expresses a SPOIL-1 receptor on the cell surface with a SPOIL-1 protein or biological portion thereof, and IL-1, to form a competitive binding assay. The binding assay can then be contacted with a test compound in order to determine the ability of the test compound to preferentially bind to the receptor as compared with the SPOIL-1 protein or biological portion thereof and/or modulate IL-1 stimulated activity by the cell.

In another embodiment, an assay is a cell-based assay comprising contacting a cell expressing a SPOIL-1 target molecule with a test compound and determining the ability of the test compound to modulate (e.g. stimulate or inhibit) the activity of the SPOIL-1 target molecule. Determining the ability of the test compound to modulate the activity of a SPOIL-1 target molecule can be accomplished, for example, by determining the ability of the SPOIL-1 protein to bind to or interact with the SPOIL-1 target molecule in the presence of the test compound. This assay can be performed in the presence of IL-1, and the ability of the SPOIL-1 protein to interact with the target molecule can be determined by assessing the activity of a cell that is normally stimulated by IL-1 as compared to a control assay comprising cell expressing a SPOIL-1 target molecule, SPOIL-1 protein and IL-1 without the test compound.

Determining the ability of the SPOIL-1 protein to bind to or interact with a SPOIL-1 target molecule can be accomplished by determining the activity of the target molecule. For example, the activity of the target molecule can be determined by detecting induction or lack of induction of a cellular second messenger of the target (i.e. intracellular $Ca^{2+}$, diacylglycerol, $IP_3$, $PGE_2$, etc.), detecting catalytic/enzymatic activity of the target an appropriate substrate, detecting the induction of a reporter gene (comprising a IL-1-responsive regulatory element operatively linked to a nucleic acid encoding a detectable marker, e.g., luciferase), or detecting a cellular response or lack of a cellular response, for example, IL-1 stimulated development, differentiation or the rate of IL-1 stimulated proliferation.

In yet another embodiment, the assay is a cell-free assay in which a SPOIL-1 protein or biologically active portion thereof is contacted with a test compound and the ability of the test compound to modulate (e.g., stimulate or inhibit) the activity of the SPOIL-1 protein or biologically active portion thereof is determined. Determining the ability of the test compound to modulate the activity of a SPOIL-1 protein can be accomplished, for example, by determining the ability of the SPOIL-1 protein to bind to a SPOIL-1 target molecule in the presence of IL-1 in the absence and presence of the test compound. Determining the ability of the SPOIL-1 protein to bind to a SPOIL-1 target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1 995) *Curr. Opin. Struct. Biol.* 5:699–705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

In an alternative embodiment, determining the ability of the test compound to modulate the activity of a SPOIL-1 protein can be accomplished by determining the ability of the SPOIL-1 protein and a SPOIL-1 target molecule to further modulate the activity of IL-1. For example, the presence or absence of an IL-1 stimulated activity can be determined as previously described.

In more than one embodiment of the above assay methods of the present invention, it may be desirable to immobilize either SPOIL-1 or its target molecule to facilitate separation of complexed from uncomplexed forms of one or both of the proteins, as well as to accommodate automation of the assay. Binding of a test compound to a SPOIL-1 protein, or interaction of a SPOIL-1 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/SPOIL-1 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or SPOIL-1 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of SPOIL-1 binding or activity determined using standard techniques.

Other techniques for immobilizing proteins on matrices can also be used in the screening assays of the invention. For example, either a SPOIL-1 protein or a SPOIL-1 target molecule can be immobilized utilizing conjugation of biotin and streptavidin. Biotinylated SPOIL-1 protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with SPOIL-1 protein or target molecules but which do not interfere with binding of the SPOIL-1 protein to its target molecule can be derivatized to the wells of the plate, and unbound target or SPOIL-1 protein trapped in the wells by antibody conjugation. Methods for detecting such complexes, in addition to those described above for the GST-immobilized complexes, include immunodetection of complexes using antibodies reactive with the SPOIL-1 protein or target molecule, as well as enzyme-linked assays which rely on detecting an enzymatic activity associated with the SPOIL-1 protein or target molecule.

In yet another aspect of the invention, the SPOIL-1 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with SPOIL-1 ("SPOIL-1-binding proteins" or "SPOIL-1-bp") and modulate SOPIL-1 activity. Such SPOIL-1-binding proteins are also likely to be involved in the propagation of signals by the SPOIL-1 proteins as, for example, downstream elements of a SPOIL-1-mediated signaling pathway. Alternatively, such SPOIL-1-binding proteins are likely to be cell-surface molecules associated with non-SPOIL-1 expressing cells, wherein such SPOIL-1-binding proteins are involved in signal transduction.

The two-hybrid system is based on the modular nature of most transcription factors, which consist of separable DNA-binding and activation domains. Briefly, the assay utilizes two different DNA constructs. In one construct, the gene that codes for a SPOIL-1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a SPOIL-1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the SPOIL-1 protein.

This invention further pertains to novel SPOIL-1 agents such as SPOIL-1 proteins or biologically active portions thereof, SPOIL-1 variants which function as IL-1 agonists and nucleic acid molecules encoding a SPOIL-1 protein or variant, which can be screened to determine the efficacy of such agents on various IL-1 stimulated activities (e.g., IL-1 stimulated immune response, IL-1 stimulated proliferation, IL-1 stimulated transduction pathway, or IL-1 stimulated differentiation).

In one embodiment, determining the ability of a SPOIL-1 agent to modulate the activity of IL-1 can be accomplished by testing the ability of SPOIL-1 to interfere with the proliferation of T cells in the presence of IL-1.

It is also within the scope of this invention to further use a SPOIL-1 agent as described herein in an appropriate animal model. For example, an agent as described herein (e.g., an IL-1 modulating agent) can be used in an animal model to determine the efficacy, toxicity, or side effects of treatment with such an agent. Alternatively, a SPOIL-1 agent identified as described herein can be used in an animal model to determine the mechanism of action of such an agent. Animal models for use in determining the efficacy or mechanism of action of a SPOIL-1 agent of the present invention include animal models demonstrating parameters of sepsis (e.g., animals injected with *E. coli* to induce hypotension) and animal models for determining bone metabolism (e.g., lethally irradiated mice which have been transplanted with SPOIL-1 infected marrow cells). Other animal models which are recognized in the art as predictive of results in humans with various IL-1 induced disorders are known in the art and described, for example, in Dinarello (1991) *Blood* 77(8):1627–1652. Furthermore, this invention pertains to uses of SPOIL-1 agents and agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the SPOIL-1 nucleotide sequences, described herein, can be used to map the location of the SPOIL-1 genes on a chromosome. The mapping of the SPOIL-1 sequences to chromosomes is an important first step in correlating these sequences with genes associated with disease. Briefly, SPOIL-1 genes can be mapped to chromosomes by preparing PCR primers (preferably 15–25 bp in length) from the SPOIL-1 nucleotide sequences. Computer analysis of the SPOIL-1 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the SPOIL-1 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the SPOIL-1 nucleotide sequences to design oligonucleotide primers, sublocalization can be achieved with panels of fragments from specific chromosomes. Other mapping strategies which can similarly be used to map a 9o, 1p, or 1v sequence to its chromosome include in situ hybridization (described in Fan, Y. et al. (1990) *PNAS*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle.

The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the SPOIL-1 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The SPOIL-1 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the SPOIL-1 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The SPOIL-1 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 (e.g., nucleotides 496 to 667) can comfortably provide positive individual identification with a panel of perhaps 10 to 1,000 primers which each yield a noncoding amplified sequence of 100 bases. If predicted coding sequences, such as those in SEQ ID NO:3 or SEQ ID NO:4 are used, a more appropriate number of primers for positive individual identification would be 500–2,000.

If a panel of reagents from SPOIL-1 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial SPOIL-1 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO: 1 (e.g., nucleotides 496 to 667) are particularly appropriate for this use as greater numbers of polymorphisms occur in the noncoding regions, making it easier to differentiate individuals using this technique. Examples of polynucleotide reagents include the SPOIL-1 nucleotide sequences or portions thereof, e.g., fragments derived from the noncoding regions of SEQ ID NO:1 (nucleotides 496 to 667), having a length of at least 20 bases, preferably at least 30 bases.

The SPOIL-1 nucleotide sequences described herein can further be used to provide polynucleotide reagents, e.g., labeled or labelable probes which can be used in, for example, an in situ hybridization technique, to identify a specific tissue, e.g., tissue from the esophagus. This can be very useful in cases where a forensic pathologist is presented with a tissue of unknown origin. Panels of such SPOIL-1 probes can be used to identify tissue by species and/or by organ type.

In a similar fashion, these reagents, e.g., SPOIL-1 primers or probes can be used to screen tissue culture for contamination (i.e. screen for the presence of a mixture of different types of cells in a culture).

C. Predictive Medicine

The present invention also pertains to the field of predictive medicine in which diagnostic assays, prognostic assays, and monitoring clinical trails are used for prognostic (predictive) purposes to thereby treat an individual prophylactically. Accordingly, one aspect of the present invention relates to diagnostic assays for determining SPOIL-1 protein and/or nucleic acid expression as well as SPOIL-1 activity, in the context of a biological sample (e.g., blood, serum, cells, tissue) to thereby determine whether an individual is afflicted with a disease or disorder, or is at risk of developing a disorder, associated with aberrant IL-1 expression or activity. The invention also provides for prognostic (or predictive) assays for determining whether an individual is at risk of developing a disorder associated with SPOIL-1 protein, nucleic acid expression or activity. For example, mutations in a SPOIL-1 gene can be assayed in a biological sample. Such assays can be used for prognostic or predictive purpose to thereby prophylactically treat an individual prior to the onset of a disorder associated with SPOIL-1 protein, nucleic acid expression or activity or characterized by aberrant IL-1 expression or activity.

Another aspect of the invention pertains to monitoring the influence of SPOIL-1 agents (e.g., SPOIL-1 proteins) on the expression or activity of IL-1 in clinical trials.

These and other agents are described in further detail in the following sections.

1. Diagnostic Assays

An exemplary method for detecting the presence or absence of SPOIL-1 protein or nucleic acid in a biological sample involves obtaining a biological sample from a test subject and contacting the biological sample with a compound or an agent capable of detecting SPOIL-1 protein or nucleic acid (e.g., mRNA, genomic DNA) that encodes SPOIL-1 protein such that the presence of SPOIL-1 protein or nucleic acid is detected in the biological sample. A preferred agent for detecting SPOIL-1 mRNA or genomic DNA is a labeled nucleic acid probe capable of hybridizing to SPOIL-1 mRNA or genomic DNA. The nucleic acid probe can be, for example, a SPOIL-1 nucleic acid molecule, such as the nucleic acid of SEQ ID NO:3, SEQ ID NO:4, or a portion thereof, such as an oligonucleotide of at least 15, 30, 50, 100, 250 or 500 nucleotides in length and sufficient to specifically hybridize under stringent conditions to SPOIL-1 mRNA or genomic DNA. Other suitable probes for use in the diagnostic assays of the invention are described herein.

A preferred agent for detecting SPOIL-1 protein is an antibody capable of binding to SPOIL-1 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect SPOIL-1 mRNA, protein, or genomic DNA in a biological sample in vitro as well as in vivo. For example, in vitro techniques for detection of SPOIL-1 mRNA include Northern hybridizations and in situ hybridizations. In vitro techniques for detection of SPOIL-1 protein include enzyme linked immunosorbent assays (ELISAs), Western blots, immunoprecipitations and immunofluorescence. In vitro techniques for detection of SPOIL-1 genomic DNA include Southern hybridizations. Furthermore, in vivo techniques for detection of SPOIL-1 protein include introducing into a subject a labeled anti-SPOIL-1 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting SPOIL-1 protein, mRNA, or genomic DNA, such that the presence of SPOIL-1 protein, mRNA or genomic DNA is detected in the biological sample, and comparing the presence of SPOIL-1 protein, mRNA or genomic DNA in the control sample with the presence of SPOIL-1 protein, mRNA or genomic DNA in the test sample.

The invention also encompasses kits for detecting the presence of SPOIL-1 in a biological sample. For example, the kit can comprise a labeled compound or agent capable of detecting SPOIL-1 protein or mRNA in a biological sample; means for determining the amount of SPOIL-1 in the sample; and means for comparing the amount of SPOIL-1 in the sample with a standard. The compound or agent can be packaged in a suitable container. The kit can further comprise instructions for using the kit to detect SPOIL-1 protein or nucleic acid.

2. Prognostic Assays

The diagnostic methods described herein can furthermore be utilized to identify subjects having or at risk of developing a disease or disorder associated with aberrant IL-1 expression or activity (as detected by the presence of SPOIL-1 ). For example, the assays described herein, such as the preceding diagnostic assays or the following assays, can be utilized to identify a subject having or at risk of developing a disorder associated with SPOIL-1 protein, nucleic acid expression or activity and/or characterized by aberrant IL-1 expression or activity such as an inflammatory disorder or an IL-1 stimulated differentiative disorder (e.g., a bone metabolism disorder). Alternatively, the prognostic assays can be utilized to identify a subject having or at risk for developing a differentiative or proliferative disease (e.g., leukemia). Thus, the present invention provides a method for identifying a disease or disorder associated with aberrant IL-1 expression or activity in which a test sample is obtained from a subject and SPOIL-1 protein or nucleic acid (e.g, mRNA, genomic DNA) is detected, wherein the presence of SPOIL-1 protein or nucleic acid is diagnostic for a subject having or at risk of developing a disease or disorder characterized aberrant IL-1 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered a SPOIL-1 agent (e.g., a SPOIL-1 protein, a SPOIL-1 peptide, or a nucleic acid molecule encoding a SPOIL-1 protein) to treat a disease or disorder associated with aberrant IL-1 expression or activity. For example, such methods can be used to determine whether a subject can be effectively treated with a SPOIL-1 agent for a disorder, such as a proinflammatory disorder or an IL-1 stimulated differentiative disorder (e.g., a bone metabolism disorder). Alternatively, such methods can be used to determine whether a subject can be effectively treated with a SPOIL-1 agent for a differentiative or proliferative disease (e.g., leukemia). Thus, the present invention provides methods for determining whether a subject can be effectively treated with a SPOIL-1 agent for a disorder associated with aberrant IL-1 expression or activity in which a test sample is obtained and SPOIL-1 protein or nucleic acid expression or activity is detected (e.g., wherein the presence of SPOIL-1 protein or nucleic acid expression or activity and/or an abundance of IL-1 expression or activity is diagnostic for a subject that can be administered the SPOIL-1 agent to treat a disorder associated with aberrant IL-1 expression or activity).

The methods of the invention can also be used to detect genetic alterations in a SPOIL-1 gene, thereby determining if a subject with the altered gene is at risk for a disorder characterized by aberrant IL-1 expression. In preferred embodiments, the methods include detecting, in a sample of cells from the subject, the presence or absence of a genetic alteration characterized by at least one of an alteration affecting the integrity of a gene encoding a SPOIL-1-protein, or the mis-expression of the SPOIL-1 gene. For example, such genetic alterations can be detected by ascertaining the existence of at least one of 1) a deletion of one or more nucleotides from a SPOIL-1 gene; 2) an addition of one or more nucleotides to a SPOIL-1 gene; 3) a substitution of one or more nucleotides of a SPOIL-1 gene, 4) a chromosomal rearrangement of a SPOIL-1 gene; 5) an alteration in the level of a messenger RNA transcript of a SPOIL-1 gene, 6) aberrant modification of a SPOIL-1 gene, such as of the methylation pattern of the genomic DNA, 7) the presence of a non-wild type splicing pattern of a messenger RNA transcript of a SPOIL-1 gene, 8) a non-wild type level of a SPOIL-1-protein, 9) allelic loss of a SPOIL-1 gene, and 10) inappropriate post-translational modification of a SPOIL-1-protein. As described herein, there are a large number of assay techniques known in the art which can be used for detecting alterations in a SPOIL-1 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the SPOIL-1-gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a SPOIL-1 gene under conditions such that hybridization and amplification of the SPOIL-1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, *Proc. Natl. Acad. Sci. USA* 87:1874–1878), transcriptional amplification system (Kwoh, D. Y. et al., 1989, Proc. Natl. Acad. Sci. USA 86:1173–1177), Q-Beta Replicase (Lizardi, P. M. et all, 1988, *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a SPOIL-1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,53 1) can be used to score for the presence of specific mutations by development or loss of a ribozyme cleavage site.

In other embodiments, genetic mutations in SPOIL-1 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–25 759). For example, genetic mutations in SPOIL-1 can be identified in two dimensional arrays containing light-generated DNA probes as described in Cronin, M. T. et al. suprca. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the SPOIL-1 gene and detect mutations by comparing the sequence of the sample SPOIL-1 with the corresponding wild-type (control) sequence. Examples of sequencing reactions include those based on techniques developed by Maxim and Gilbert ((1977) *PNAS* 74:560) or Sanger ((1977) *PNAS* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the SPOIL-1 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type SPOIL-1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation.

See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in SPOIL-1 cDNAs obtained from samples of cells. For example, the mutY enzyme of *E. coli* cleaves A at G/A mismatches and the thymidine DNA glycosylase from Hela cells cleaves T at G/T mismatches (Hsu et al. (1994) *Carcinogenesis* 15:1657–1662). According to an exemplary embodiment, a probe based on a SPOIL-1 sequence, e.g., a wild-type SPOIL-1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in SPOIL-1 genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1 993) *Mutat Res* 285:125–144; and Hayashi (1992) *Genet Anal Tech Appl* 9:73–79). Single-stranded DNA fragments of sample and control SPOIL-1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki etal. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3 end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a SPOIL-1 gene.

Furthermore, any cell type or tissue in which SPOIL-1 is expressed may be utilized in the prognostic assays described herein.

3. Monitoring of Effects During Clinical Trials

Monitoring the influence of SPOIL-1 agents (e.g., SPOIL-1 proteins) on the expression or activity of IL-1 (e.g., modulation of IL-1 dependent signal transduction, modulation of IL-1 stimulated cell development or differentiation, regulation of IL-1 stimulated cellular proliferation) can be applied not only in basic drug screening, but also in clinical trials. For example, the effectiveness of a SPOIL-1 agent determined by a screening assay (as described herein) to decrease or increase IL-1 expression or activity can be monitored in clinical trails of subjects exhibiting increased IL-1 expression or activity and/or decreased SPOIL-1 gene expression, protein levels or activity. Alternatively, the effectiveness of a SPOIL-1 agent determined by a screening assay to increase IL-1 expression or activity and/or down-regulate SPOIL-1 gene expression, protein levels or activity, can be monitored in clinical trails of subjects exhibiting increased IL-1 expression or activity and/or decreased SPOIL-1 gene expression, protein levels or activity. In such clinical trials, the expression or activity of IL-1 and, preferably, other genes that have been implicated in, for example, a proinflammatory disorder or a bone metabolism disorder can be used as a "read out" or markers of the phenotype of a particular cell.

For example, and not by way of limitation, treatment with a SPOIL-1 agent (e.g., SPOIL-1 protein, peptide, or nucleic acid molecule encoding a SPOIL-1 protein) which modulates IL-1 activity (e.g., identified in a screening assay as described herein) can be identified. Thus, to study the effect of SPOIL-1 agents on IL-1 stimulated proliferative disorders (e.g., proinflammatory disorder) or IL-1 stimulated developmental or differentiative disorder (e.g., a bone metabolism disorder), for example, in a clinical trial, cells can be isolated and RNA prepared and analyzed for the levels of expression of IL-1 and other genes implicated in an IL-1 stimulated proliferative disorder or IL-1 stimulated developmental or differentiative disorder, respectively. The levels of IL-1 expression or activity can be quantified, for example, by measuring the amount of protein produced (by one of the methods as described herein) or by measuring the levels of activity of SPOIL-1 or other genes. In this way, SPOIL-1 expression or level of expression of other genes or proteins involved in IL-1 stimulated activities can serve as a marker, indicative of the physiological response of the cells to the SPOIL-1 agent. In a non-limiting example, by staining for tartrate resistant acid phosphatase (TRAP), the level of osteoclasts present in a sample can be measured since the IL-1 serves as a stimulator for osteoclast production. Decreased numbers of osteoclasts serve as an indicator that a SPOIL-1 agent is inhibiting bone resorption. Accordingly, this response state may be determined before, and at various points during treatment of the individual with the SPOIL-1 agent.

In a preferred embodiment, the present invention provides a method for monitoring the effectiveness of treatment of a subject with a SPOIL-1 agent (e.g., an SPOIL-1 protein, SPOIL-1 peptide, SPOIL-1 variant-IL-1 agonist, or other agent described herein) comprising the steps of (i) obtaining a pre-administration sample from a subject prior to administration of the agent; (ii) detecting the level of expression of a IL-1 or other protein, mRNA, or genomic DNA indicative of IL-1 activity in the preadministration sample; (iii) obtaining one or more post-administration samples from the subject; (iv) detecting the level of expression or activity of the IL-1 or other protein, mRNA, or genomic DNA IL-1 indicator in the post-administration samples; (v) comparing the level of expression or activity of IL-1 or the protein, mRNA, or genomic DNA which indicate the presence or absence of IL-1 activity in the pre-administration sample with the levels in the post administration sample or samples; and (vi) altering the administration of the SPOIL-1 agent to the subject accordingly. For example, decreased administration of the SPOIL-1 agent may be desirable to increase IL1 expression or activity to higher levels than detected, i.e. to decrease the effectiveness of the SPOIL-1 agent. Alternatively, increased administration of the SPOIL-1 agent may be desirable to decrease the expression or activity of IL-1 to lower levels than detected, i.e., to increase the effectiveness of the SPOIL-1 agent. According to such an embodiment, IL-1 expression or activity may be used as an indicator of the effectiveness of a SPOIL-1 agent, even in the absence of an observable phenotypic response.

D. Methods of Treatment

The present invention provides for both prophylactic and therapeutic methods of treating a subject at risk of (or susceptible to) a disorder or having a disorder associated with aberrant IL-1 expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the SPOIL-1 molecules of the present invention or SPOIL-1 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant IL-1 expression or activity, by administering to the subject a SPOIL-1 agent which modulates at least one IL-1 activity. Subjects at risk for a disease which is caused or contributed to by aberrant IL-1 expression or activity can be identified by, for example, any or a combination of diagnostic or prognostic assays as described herein. Administration of a prophylactic agent can occur prior to the manifestation of symptoms characteristic of the IL-1 aberrancy, such that a disease or disorder is prevented or, alternatively, delayed in its progression. Depending on the type of IL-1 aberrancy, for example, a SPOIL-1 protein or SPOIL-1 variant-IL-1 agonist agent can be used for treating the subject. The appropriate SPOIL-1 agent can be determined based on screening assays described herein. The prophylactic methods of the present invention are further discussed in the following subsections.

2. Therapeutic Methods

Another aspect of the invention pertains to methods of modulating IL-1 expression or activity for therapeutic purposes. The modulatory method of the invention involves contacting a cell with a SPOII-I agent that modulates one or more of the activities of IL-1 activity associated with the cell or one or more of the activities involved with bone wasting. A SPOIL-1 agent that modulates IL-1 activity can be an agent as described herein, such as a nucleic acid encoding a SPOIL-1 protein or a SPOIL-1 protein, a SPOIL-1 peptide, a SPOIL-1 peptidomimetic. In one embodiment, the SPOIL-1 agent stimulates one or more IL-1 protein activity. Examples of such stimulatory agents include active SPOIL-1 variant which serves as an IL-1 agonist and a nucleic acid molecule encoding such a SPOIL-1 variant that has been introduced into the cell. In another embodiment, the SPOIL-1 agent inhibits one or more IL-1 activity. Examples of such inhibitory agents include SPOIL-1 proteins and nucleic acid molecules encoding a SPOIL-1 protein. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant IL-1 expression or activity. In one embodiment, the method involves administering a SPOIL-1 agent (e.g., an agent described herein), or combination of agents that modulates (e.g., upregulates or downregulates) IL-1 expression or activity. In another embodiment, the method involves administering a SPOIL-1 protein or nucleic acid molecule as therapy to compensate for reduced SPOIL-1 expression or activity.

Stimulation of IL-1 activity is desirable in situations in which IL-1 is abnormally downregulated and/or in which increased IL-1 activity is likely to have a beneficial effect. Likewise, inhibition of IL-1 activity is desirable in situations in which IL-1 is abnormally upregulated and/or in which decreased IL-1 activity is likely to have a beneficial effect. One example of such a situation is where a subject has a disorder characterized by aberrant IL-1 stimulated cellular differentiation (e.g., a bone resorption disorder). Another example of such a situation is where the subject has a proinflammatory disorder (e.g., sepsis) characterized by an aberrant IL-1 response.

3. Pharmacogenomics

The SPOIL-1 molecules of the present invention which have a stimulatory or inhibitory effect on IL-1 activity (e.g., IL-1 stimulated cellular responses) as identified by a screening assay described herein can be administered to individuals to treat (prophylactically or therapeutically) disorders (e.g, IL-1 stimulated inflammatory or developmental disorders) associated with aberrant IL-1 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a SPOIL-1 molecule or SPOIL-1 modulator as well as tailoring the dosage and/or therapeutic regimen of treatment with a SPOIL-1 molecule or SPOIL-1 modulator.

Pharmacogenomics deals with clinically significant hereditary variations in the response to drugs due to altered drug disposition and abnormal action in affected persons. See e.g., Eichelbaum, M., *Clin Exp Pharmacol Physiol*, 1996, 23(10–11):983–985 and Linder, M. W., *Clin Chem*, 1997, 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA.

For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug target is known (e.g., a SPOIL-1 protein or SPOIL-1 receptor of the present invention), all common variants of that gene can be identified in the population and a particular drug response can be associated with one or more genes.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C 19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.]

Alternatively, a method termed the "gene expression profiling", can be utilized to identify genes that predict drug response. For example, the gene expression of an animal dosed with a drug (e.g., a SPOIL-1 molecule or SPOIL-1 modulator of the present invention) indicate whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a SPOIL-1 molecule or SPOIL-1 modulator, such as a modulator identified by one of the exemplary screening assays described herein.

This invention is further illustrated by the following examples which should not be construed as limiting. The contents of all references, patents and published patent applications cited throughout this application are incorporated herein by reference.

EXAMPLES

Example 1

Isolation and Characterization of Murine SPOIL-1 cDNA

In this example, the isolation of the gene encoding murine SPOIL-1 (also referred to as "TANGO 080") is described.

A murine SPOIL-1 cDNA was identified by searching with a murine cDNA encoding an IL-1 signature region (Prosite™ Accession Number PDOC00226) against a copy of the GenBank nucleotide database using the BLASTN™ program (BLASTN 1.3MP: Altschul et al., *J. Mol. Bio.* 215:403, 1990). A clone with 48% homology with the murine cDNA IL-1 signature region was found by this search. The sequence was analyzed against a non-redundant protein database with the BLASTX™ program, which translates a nucleic acid sequence in all six frames and compares it against available protein databases (BLASTX 1.3MP:Altschul et al., supra). This protein database is a combination of the SwissProt, PIR, and NCBI GenPept protein databases. One clone was obtained from the IMAGE consortium, and fully sequenced. The additional sequencing of this clone extended the original EST by 267 nucleotides at both the 5' and 3' ends. The cDNA for this clone is approximately 746 nucleotides in length and has an open reading frame of 297 nucleotides that is predicted to encode a protein of 98 amino acids.

The original first pass sequence of the clone showed homology to horse IL-1ra and murine IL-1ra using the BLASTX™ program. The nucleotide sequence and predicted amino acid sequence are shown in FIG. 1 (corresponding to SEQ ID NO:1 and SEQ ID NO:2, respectively). The SPOIL-1 protein (corresponding to amino acids 1–98 of the predicted amino acid sequence, SEQ ID NO:2) shows 37.0% identity to the horse IL-1ra protein and 39.0% identity to the murine IL-1ra protein (see FIG. 3). The percent identity was calculated using the alignment generated using MegAlign™ sequence alignment software. The initial pairwise alignment step was performed using a Wilbur-Lipmann algorithm with a K-tuple of 1, a GAP penalty of 3, a window of 5, and diagonals saved set to=5. The multiple alignment step was performed using the Clustal algorithm with a PAM 250 residue weight Table, a GAP penalty of 10, and a GAP length penalty of 10.

Alignment of murine SPOIL-1 protein with murine IL-1α (SwissProt™ Accession Number P01582) and murine IL-1β (SwissProt™ Accession Number P10749) (see FIG. 3) indicates the presence of an aspartic acid at amino acid residue 91 of SEQ ID NO: 2 and amino acid residue 74 of SEQ ID NO:5 which corresponds to an aspartic acid found at amino acid residue 266 of murine IL-1α and amino acid residue 261 of murine IL-1β. In addition, alignment of murine SPOIL-1 with murine IL-1ra indicates that this aspartic acid residue of SPOIL-1 corresponds with a lysine at amino acid residue 171 of murine IL-1ra (or amino acid residue 145 of mature murine IL-1ra) which has been shown to convert IL-1ra into an agonist by mutating this lysine residue to an aspartic acid residue. (Ju et al. (1991) *Proc. Natl Acad. Sci. USA* 88:2658–2662).

This murine SPOIL-1 protein contains an IL-1 signature domain (corresponding to amino acids 58–80 of the predicted amino acid sequence, SEQ ID NO:2 and amino acids 41–63 of SEQ ID NO:5) and a signal sequence (corresponding to amino acids 1–17 of the predicted amino acid sequence, SEQ ID NO:2) which is cleaved to form a mature SPOIL-1 protein (corresponding to amino acids 1–81 of SEQ ID NO:5). The predicted molecular weight for the 98 amino acid SPOIL-1 is approximately 10.96 kDa and the predicted molecular weight for mature SPOIL-1 (SEQ ID NO:5) is approximately 9.1 kDa.

A BLASTN™ search of the EST database revealed the following ESTs having significant homology to clone Accession # AA03024:

| EST Database hits | Species | Base Pairs Covered | % Identity | Coding? |
|---|---|---|---|---|
| Accession # W78043 | human | 210–338 | 60 | yes |
| Accession # X64532 | human | 211–338 | 61 | yes |

Example 2

Distribution of SPOIL-1 mRNA In Mouse Tissues
In Situ Hybridization Analysis

In situ analysis revealed the following expression patterns when tissue sections were hybridized with SPOIL-1 probes. SPOIL-1 mRNA was expressed almost exclusively in the squamous epithelium of the oesophagus in both adult and embryonic mouse tissues. SPOIL-1 mRNA was also expressed in the epithelial lining of the mouth in adult mouse tissues and embryonic mouse tissues.

Example 3

Expression of Recombinant SPOIL-1 Protein in Bacterial Cells

SPOIL-1 can be expressed as a recombinant glutathione-S-transferase (GST) fusion polypeptide in *E. coli* and the fusion polypeptide can be isolated and characterized. Specifically, SPOIL-1 is fused to GST and this fusion polypeptide is expressed in *E. coli*, e.g., strain PEB199. As the murine SPOIL-1 protein is predicted to be approximately 9.1 kDa and the GST is predicted to be approximately 26 kDa, the fusion polypeptide is predicted to be approximately 35.1kDa in molecular weight. Expression of the GST-SPOIL-1 fusion protein in PEB199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 4

Expression of Recombinant SPOIL-1 Protein in COS Cells

To express the SPOIL-1 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire SPOIL-1 protein and a HA tag (Wilson et al. (1984) Cell 37:767) fused in-frame to its 3' end of the fragment is cloned into the polylinker region of the vector, thereby placing the expression of the recombinant protein under the control of the CMV promoter.

To construct the plasmid, the SPOIL-1 DNA sequence is amplified by PCR using two primers. The 5' primer contains the restriction site of interest followed by approximately twenty nucleotides of the SPOIL-1 coding sequence starting from the initiation codon; the 3' end sequence contains complementary sequences to the other restriction site of interest, a translation stop codon, the HA tag and the last 20 nucleotides of the SPOIL-1 coding sequence. The PCR amplified fragment and the pCDNA/Amp vector are digested with the appropriate restriction enzymes and the vector is dephosphorylated using the CIAP enzyme (New England Biolabs, Beverly, MA). Preferably the two restriction sites chosen are different so that the SPOIL-1 gene is inserted in the correct orientation. The ligation mixture is transformed into *E. coli* cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the SPOIL-1-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the SPOIL-1 protein is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated proteins are then analyzed by SDS-PAGE.

Alternatively, DNA containing the SPOIL-1 coding sequence is cloned directly into the polylinker of the pCDNA/Amp vector using the appropriate restriction sites. The resulting plasmid is transfected into COS cells in the manner described above, and the expression of the SPOIL-1 protein is detected by radiolabelling and immunoprecipitation using a SPOIL-1 specific monoclonal antibody Example 5

Retroviral Delivery of SPOIL-1

Full length murine SPOIL-1 can be expressed in vivo mediated by retroviral infection. For example, the sequence for murine SPOIL-1 (amino acids 1–98) was amplified using the following primers;

Forward Primer (SEQ ID NO:8):
5' AAAAAAGAAT TCGCCACCAT GTTCAGGATC TTA 3'

Reverse Primer (SEQ ID NO:9):
5' TCCTCTGTCG ACTCACTTGT CGTCGTCGTC CTTGTAGTCA TGTACCACAATCAT 3'

The reverse primer places an epitope tag (Flag sequence) on the 3' end of the protein. Amplified products were then subcloned into the retroviral vector MSCVneo (Hawley et al. (1994) *Gene Therapy* 1:136–138), and sequence verified. Bone marrow from 5-fluorouracil treated mice infected with the retrovirus is then transplanted into irradiated mouse recipients and pathology reviewed after 5 weeks.

The spleen and bones of the mouse recipient were taken 5 weeks after transplantation. Disassociated spleen cells, which are a source of osteoclast progenitors, from the SPOIL-1 infected mice were plated on top of ST2 bone marrow stromal line in the presence of 1, 25 dihdroxyvitamin D3 as described by Lacey et al. (1995) *Endocrinology* 136:2367–2376 and Udagawa et al. (1989) *Endocrinology* 125:1805–1813. In addition, spleen cells from control mice transplanted with marrow infected with retrovirus without the inserted SPOIL-1 gene, were plated. After nine days of culture, the number of osteoclasts was determined by staining for tartrate resistant acid phosphatase (TRAP).

The results of this experiment demonstrated that the number of TRAP positive osteoclasts was dramatically decreased in cultures with the SPOIL-1 infected spleen cells than with the control cells. Histologically, the bones of mice recipients transplanted with TANGO infected marrow, also appeared to be thicker than the bones of the corresponding control mice. Generally, there was less trabecular bone at the growth plate. The trabecular bone was compressed and thickened with more osteoloid formation and more osteoblasts present.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. An isolated nucleic acid molecule comprising the nucleotide sequence of SEQ ID NO:1.

2. An isolated nucleic acid molecule consisting of the nucleotide sequence of SEQ ID NO:1.

3. An isolated nucleic acid molecule consisting of the nucleotide sequence of SEQ ID NO:3.

4. The nucleic acid molecule of claim 1, further comprising heterologous nucleic acid sequences.

5. A vector comprising the nucleic acid molecule of claim 1.

6. A vector comprising the nucleic acid molecule of claim 4.

7. The vector of claim 5, which includes nucleic acid sequences which regulate expression of a polypeptide encoded by the nucleic acid molecule.

8. The vector of claim 6, which includes nucleic acid sequences which regulate expression of a polypeptide encoded by the nucleic acid molecule.

9. A host cell comprising the vector of claim 5.

10. A host cell comprising the vector of claim 6.

11. A host cell comprising the nucleic acid molecule of claim 1.

12. The host cell of claim 9 which is a mammalian host cell.

13. The host cell of claim 10 which is a mammalian host cell.

14. The host cell of claim 11 which is a mammalian host cell.

15. A method for producing a polypeptide comprising culturing the host cell of claim 11 in a suitable medium such that the polypeptide is produced.

16. An isolated nucleic acid molecule consisting of the nucleotide sequence of SEQ ID NO:4.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 746 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 135..428

(xi) SEQUENCE DESCRIPTION: SEQ ID NO:1:

```
GAATTCGGCA CGAGGGTAGT GTGCAGACAC ATTCCTATTC AATCAGGGTC AATCTGCAGA       60

TTGGCAGCTC AGAAACAACA TCACCATAAT GAATAAGGAG AAAGAACTAA GAGCAGCATC      120

ACCTTCGCTT AGAC ATG TTC AGG ATC TTA GTA GTC GTG TGT GGA TCC TGC        170
              Met Phe Arg Ile Leu Val Val Val Cys Gly Ser Cys
                1           5                  10

AGA ACA ATA TCC TCA CTG CAG TCC CAA GGA AAG AGC AAA CAG TTC CAG        218
Arg Thr Ile Ser Ser Leu Gln Ser Gln Gly Lys Ser Lys Gln Phe Gln
            15                  20                  25

GAA GGG AAC ATA ATG GAA ATG TAC AAC AAA AAG GAA CCT GTA AAA GCC        266
Glu Gly Asn Ile Met Glu Met Tyr Asn Lys Lys Glu Pro Val Lys Ala
        30                  35                  40

TCT CTC TTC TAT CAC AAG AAG AGT GGT ACA ACC TCT ACA TTT GAG TCT        314
Ser Leu Phe Tyr His Lys Lys Ser Gly Thr Thr Ser Thr Phe Glu Ser
45                  50                  55                  60

GCA GCC TTC CCT GGT TGG TTC ATC GCT GTC TGC TCT AAA GGG AGC TGC        362
Ala Ala Phe Pro Gly Trp Phe Ile Ala Val Cys Ser Lys Gly Ser Cys
                65                  70                  75

CCA CTC ATT CTG ACC CAA GAA CTG GGG GAA ATC TTC ATC ACT GAC TTC        410
Pro Leu Ile Leu Thr Gln Glu Leu Gly Glu Ile Phe Ile Thr Asp Phe
            80                  85                  90

GAG ATG ATT GTG GTA CAT TAAGGTTTTT AGACACATTG CTCTGTGGCA               458
Glu Met Ile Val Val His
                95

CTCTCTCAAG ATTTCTTGGA TTCTAACAAG AAGCAATCAA AGACACCCCT AACAAAATGG      518

AAGACTGAAA AGAAAGCTGA GCCCTCCCTG GGCTGTTTTT CCTTGGTGGT GAATCAGATG      578

AAGAACATCT TACCATGTTT TCATCCAAAG CATTTACTGT TGGTTTTTAC AAGGAGTGAA      638

TTTTTTAAAA TAAAATCATT TATCTCATAA AAAAAAAAAA AAAAAAAAA AAAAAAAAA        698
```

```
AAAAAAAAAA AAAAAAAAAA AAAAAAAAAA AAAAACTCTC GCGGCCGC                        746
```

(2) INFORMATION FOR SEQ ID NO:2:

(i) SEQUENCE CHARACTERISTICS:
        (A) LENGTH: 98 amino acids
        (B) TYPE: amino acid
        (D) TOPOLOGY: linear (ii) MOLECULE TYPE: protein (xi) SEQUENCE DESCRIPTION: SEQ ID NO:2:

```
Met Phe Arg Ile Leu Val Val Val Cys Gly Ser Cys Arg Thr Ile Ser
 1               5                  10                  15

Ser Leu Gln Ser Gln Gly Lys Ser Lys Gln Phe Gln Glu Gly Asn Ile
            20                  25                  30

Met Glu Met Tyr Asn Lys Lys Glu Pro Val Lys Ala Ser Leu Phe Tyr
        35                  40                  45

His Lys Lys Ser Gly Thr Thr Ser Thr Phe Glu Ser Ala Ala Phe Pro
    50                  55                  60

Gly Trp Phe Ile Ala Val Cys Ser Lys Gly Ser Cys Pro Leu Ile Leu
65                  70                  75                  80

Thr Gln Glu Leu Gly Glu Ile Phe Ile Thr Asp Phe Glu Met Ile Val
                85                  90                  95

Val His
```

(2) INFORMATION FOR SEQ ID NO:3:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..294

(xi) SEQUENCE DESCRIPTION: SEQ ID NO:3:

```
ATG TTC AGG ATC TTA GTA GTC GTG TGT GGA TCC TGC AGA ACA ATA TCC         48
Met Phe Arg Ile Leu Val Val Val Cys Gly Ser Cys Arg Thr Ile Ser
 1               5                  10                  15

TCA CTG CAG TCC CAA GGA AAG AGC AAA CAG TTC CAG GAA GGG AAC ATA         96
Ser Leu Gln Ser Gln Gly Lys Ser Lys Gln Phe Gln Glu Gly Asn Ile
            20                  25                  30

ATG GAA ATG TAC AAC AAA AAG GAA CCT GTA AAA GCC TCT CTC TTC TAT        144
Met Glu Met Tyr Asn Lys Lys Glu Pro Val Lys Ala Ser Leu Phe Tyr
        35                  40                  45

CAC AAG AAG AGT GGT ACA ACC TCT ACA TTT GAG TCT GCA GCC TTC CCT        192
His Lys Lys Ser Gly Thr Thr Ser Thr Phe Glu Ser Ala Ala Phe Pro
    50                  55                  60

GGT TGG TTC ATC GCT GTC TGC TCT AAA GGG AGC TGC CCA CTC ATT CTG        240
Gly Trp Phe Ile Ala Val Cys Ser Lys Gly Ser Cys Pro Leu Ile Leu
65                  70                  75                  80

ACC CAA GAA CTG GGG GAA ATC TTC ATC ACT GAC TTC GAG ATG ATT GTG        288
Thr Gln Glu Leu Gly Glu Ile Phe Ile Thr Asp Phe Glu Met Ile Val
                85                  90                  95

GTA CAT                                                                 294
Val His
```

(2) INFORMATION FOR SEQ ID NO:4:

(i) SEQUENCE CHARACTERISTICS:
        (A) LENGTH: 243 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..243

(xi) SEQUENCE DESCRIPTION: SEQ ID NO:4:

```
CTG CAG TCC CAA GGA AAG AGC AAA CAG TTC CAG GAA GGG AAC ATA ATG      48
Leu Gln Ser Gln Gly Lys Ser Lys Gln Phe Gln Glu Gly Asn Ile Met
 1               5                  10                  15

GAA ATG TAC AAC AAA AAG GAA CCT GTA AAA GCC TCT CTC TTC TAT CAC      96
Glu Met Tyr Asn Lys Lys Glu Pro Val Lys Ala Ser Leu Phe Tyr His
             20                  25                  30

AAG AAG AGT GGT ACA ACC TCT ACA TTT GAG TCT GCA GCC TTC CCT GGT     144
Lys Lys Ser Gly Thr Thr Ser Thr Phe Glu Ser Ala Ala Phe Pro Gly
         35                  40                  45

TGG TTC ATC GCT GTC TGC TCT AAA GGG AGC TGC CCA CTC ATT CTG ACC     192
Trp Phe Ile Ala Val Cys Ser Lys Gly Ser Cys Pro Leu Ile Leu Thr
     50                  55                  60

CAA GAA CTG GGG GAA ATC TTC ATC ACT GAC TTC GAG ATG ATT GTG GTA     240
Gln Glu Leu Gly Glu Ile Phe Ile Thr Asp Phe Glu Met Ile Val Val
 65                  70                  75                  80

CAT                                                                 243
His
```

(2) INFORMATION FOR SEQ ID NO:5:

(i) SEQUENCE CHARACTERISTICS:
        (A) LENGTH: 81 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:5:

```
Leu Gln Ser Gln Gly Lys Ser Lys Gln Phe Gln Glu Gly Asn Ile Met
 1               5                  10                  15

Glu Met Tyr Asn Lys Lys Glu Pro Val Lys Ala Ser Leu Phe Tyr His
             20                  25                  30

Lys Lys Ser Gly Thr Thr Ser Thr Phe Glu Ser Ala Ala Phe Pro Gly
         35                  40                  45

Trp Phe Ile Ala Val Cys Ser Lys Gly Ser Cys Pro Leu Ile Leu Thr
     50                  55                  60

Gln Glu Leu Gly Glu Ile Phe Ile Thr Asp Phe Glu Met Ile Val Val
 65                  70                  75                  80

His
```

(2) INFORMATION FOR SEQ ID NO:6:

(i) SEQUENCE CHARACTERISTICS:
        (A) LENGTH: 11 amino acids
        (B) TYPE: amino acid
        (D) TOPOLOGY: linear

```
        (ii) MOLECULE TYPE: protein (v) FRAGMENT TYPE: internal (ix) FEATURE:
             (A) NAME/KEY: protein
             (B) LOCATION: 2,5,6,8,9,10
             (D) OTHER INFORMATION: /note= "Xaa is any amino acid"

(xi) SEQUENCE DESCRIPTION: SEQ ID NO:6:

Phe Xaa Ser Ala Xaa Xaa Pro Xaa Xaa Xaa Leu
1               5                   10

(2) INFORMATION FOR SEQ ID NO:7:

(i) SEQUENCE CHARACTERISTICS:
             (A) LENGTH: 11 amino acids
             (B) TYPE: amino acid
             (D) TOPOLOGY: linear (ii) MOLECULE TYPE: protein (v) FRAGMENT TYPE: internal (ix) FEATURE:
             (A) NAME/KEY: protein
             (B) LOCATION: 2
             (D) OTHER INFORMATION: /note= "Xaa is either Threonine
                 or Glutamic Acid"
             (A) NAME/KEY: protein
             (B) LOCATION: 5
             (D) OTHER INFORMATION: /note= "Xaa is either Alanine or
                 Glutamic Acid"
             (A) NAME/KEY: protein
             (B) LOCATION: 6,8, 10
             (D) OTHER INFORMATION: /note= "Xaa is any amino acid"
             (A) NAME/KEY: protein
             (B) LOCATION: 9
             (D) OTHER INFORMATION: /note= "Xaa is either Tryptophan
                 or Leucine"

(xi) SEQUENCE DESCRIPTION: SEQ ID NO:7:

Phe Xaa Ser Ala Xaa Xaa Pro Xaa Xaa Xaa Leu
1               5                   10

(2) INFORMATION FOR SEQ ID NO:8:

(i) SEQUENCE CHARACTERISTICS:
             (A) LENGTH: 33 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:8:

AAAAAAGAAT CGCCACCAT GTTCAGGATC TTA                                     33

(2) INFORMATION FOR SEQ ID NO:9:

(i) SEQUENCE CHARACTERISTICS:
             (A) LENGTH: 54 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:9:

TCCTCTGTCG ACTCACTTGT CGTCGTCGTC CTTGTAGTCA TGTACCACAA TCAT             54
```